United States Patent
Chiang et al.

(10) Patent No.: US 9,598,381 B2
(45) Date of Patent: Mar. 21, 2017

(54) SMYD2 INHIBITORS

(71) Applicant: AbbVie Inc., North Chicago, IL (US)

(72) Inventors: Gary G. Chiang, San Diego, CA (US); William N. Pappano, Libertyville, IL (US); Ramzi F. Sweis, Lake Bluff, IL (US); Zhi Wang, Libertyville, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 14/812,726

(22) Filed: Jul. 29, 2015

(65) Prior Publication Data

US 2016/0031838 A1 Feb. 4, 2016

Related U.S. Application Data

(60) Provisional application No. 62/031,499, filed on Jul. 31, 2014.

(51) Int. Cl.
| | | |
|---|---|---|
| *C07D 209/40* | (2006.01) | |
| *C07D 265/36* | (2006.01) | |
| *C07D 295/13* | (2006.01) | |
| *C07D 487/04* | (2006.01) | |
| *C07D 401/12* | (2006.01) | |
| *C07D 471/04* | (2006.01) | |
| *C07C 255/58* | (2006.01) | |

(52) U.S. Cl.
CPC .......... *C07D 265/36* (2013.01); *C07C 255/58* (2013.01); *C07D 209/40* (2013.01); *C07D 295/13* (2013.01); *C07D 401/12* (2013.01); *C07D 471/04* (2013.01); *C07D 487/04* (2013.01); *C07C 2101/14* (2013.01)

(58) Field of Classification Search
CPC .. C07D 209/40; C07D 265/36; C07D 295/13; C07D 487/04; C07D 401/12; C07D 471/04
USPC .............................. 514/230.5; 544/105
See application file for complete search history.

(56) References Cited

U.S. PATENT DOCUMENTS 8,178,570 B2 * 5/2012 Chen .................. A61K 31/4439
514/256

FOREIGN PATENT DOCUMENTS

| GB | WO 2008075025 A1 * | 6/2008 | .......... C07C 233/43 |
| WO | WO 2004091480 A2 * | 10/2004 | ......... A61K 31/4439 |
| WO | 2008075025 A1 | 6/2008 | |

OTHER PUBLICATIONS

Ferguson A.D., et al., "Structural Basis of Substrate Methylation and Inhibition of SMYD2," Structure, 2011, vol. 19 (9), pp. 1262-1273.
Huang J., et al., "Repression of p53 Activity by Smyd2-Mediated Methylation," Nature, 2006, vol. 444 (7119), pp. 629-632.
Komatsu S., et al., "Overexpression of SMYD2 Relates to Tumor Cell Proliferation and Malignant Outcome of Esophageal Squamous Cell Carcinoma," Carcinogenesis, 2009, vol. 30 (7), pp. 1139-1146.

* cited by examiner

*Primary Examiner* — Kahsay Habte
(74) *Attorney, Agent, or Firm* — Changxia Sun

(57) ABSTRACT

The present disclosure generally relates to compounds having cellular anti-proliferative activities, and more particularly relates to compounds which inhibit the activity of human SMYD2, a SET and MYND domain-containing protein lysine methyltransferase.

18 Claims, No Drawings

SMYD2 INHIBITORS

CROSS-REFERENCE TO RELATED APPLICATIONS

The present application claims priority to U.S. Provisional Patent Application No. 62/031,499, filed Jul. 31, 2014, which is hereby incorporated by reference in its entirety for all purposes.

FIELD OF THE DISCLOSURE

The present disclosure generally relates to compounds having cellular anti-proliferative activities, and more particularly relates to compounds which inhibit the activity of human SMYD2, a SET and MYND domain-containing protein lysine methyltransferase.

BACKGROUND OF THE INVENTION

The human SMYD (SET and MYND domain-containing protein) family of protein lysine methyltransferases contains five members (SMYD1-5). The role each of these protein lysine methyltransferases play in the development of cancer have been the focus of extensive study to-date. In particular, SMYD2 has been shown to methylate both histone (H2B, H3, and H4) and nonhisione protein substrates, including the tumor suppressor proteins p53 and Rb. (See, e.g., Ferguson et al., *Structure*, vol. 19, pp. 1262-1273 (2011); Komatsu et al., *Carcinogenesis*, vol. 30, pp. 1139-1146 (2009); and, Huang et al., *Nature*, vol. 444, pp. 629-632 (2006).) Methylation of K370 of p53 impairs its ability to bind to the promoters of target genes. Methylation of Rb at residue K860 generates an epitope that is selectively recognized by the transcriptional repressor L3MBTL1. This may provide a mechanism for recruiting L3MBTL1 to the promoters of specific Rb/E2F target genes, thereby repressing their activities. In addition to these established biological pathways, the SMYD2 gene lies in the 1q32-q41 region, which is frequently amplified in esophageal squamous cell carcinoma (ESCC) and other solid tumors. Overexpression of SMYD2 is observed in the esophageal cell line KYSE150, and in ESCC primary tumor samples. Genetic knockdown of SMYD2 leads to decreased ESCC cell proliferation.

Protein lysine methyltransferases have emerged as attractive targets for drug discovery. As a result, there are ongoing efforts to identify chemical starting points for this novel class of enzymes. Given the activity of SMYD2 in ESCC cells, and that its protein substrates, including the key tumor suppressors p53 and Rb, have been implicated in gene transcription, apoptosis, and cell cycle regulation, there is a need for the development of small molecule inhibitors of SMYD2.

SUMMARY OF THE DISCLOSURE

Among the provisions of the present disclosure may be noted a compound of Formula (I):

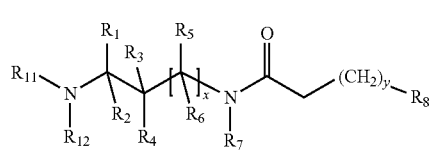

or a pharmaceutically acceptable salt thereof, wherein: each of $R_1$, $R_2$, $R_3$, $R_4$, $R_5$, and $R_6$ are independently hydrogen or $C_{1-6}$ alkyl; x has a value from 0 to 1; y has a value from 0 to 3; $R_7$ is a $C_4$-$C_6$ cycloalkyl; $R_3$ is —$OR_9$ or —$NHR_{10}$; $R_9$ is a $C_{1-10}$ alkyl; $R_{10}$ is a $C_{1-2}$ alkyl substituted with a phenyl, wherein the phenyl is optionally further substituted with halogen; and, (i) $R_{11}$ and $R_{12}$ are taken together with the nitrogen atom to which they are bound to form a 4-6 member, optionally substituted heterocyclic ring; or alternatively, (ii) one of $R_{11}$ and $R_{12}$ is hydrogen, and the other is selected from: (a) a pyrazolopyrimidinyl ring having a structure:

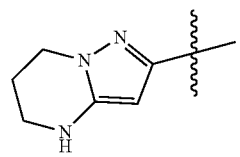 [SMILES: *c1cc2n(n1)CCCN2]

and being optionally substituted with one or more $C_{1-5}$ alkyl substituents; and, (b) a $C_{1-3}$ substituted alkyl or a $C_{1-3}$ substituted hydoxyalkyl, wherein said substituent is selected from the group consisting of piperidinyl, pyrrolidinyl, cyanophenyl, methylindolizinyl, and a moiety having a structure:

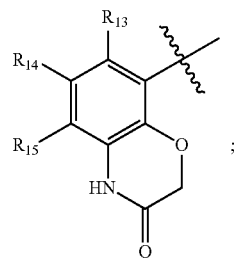

wherein $R_{13}$, $R_{14}$, and $R_{15}$ are each independently selected from hydrogen, halogen, hydroxyl, trifluoromethyl, cyano, carboxyl, $C_{1-6}$ alkyl, $C_{1-6}$ alkoxy, and $C_{1-6}$ alkylcarbonyl; provided that if one of $R_{11}$ and $R_{12}$ is $C_{1-3}$ substituted alkyl and $R_{15}$ is hydroxyl, then $R_7$ comprises a $C_4$ or $C_5$ unsubstituted cycloalkyl, or $R_8$ is —$OR_9$, or $R_8$ is —$NHR_{10}$, wherein $R_{10}$ is methyl substituted with a phenyl, optionally further substituted with a halogen.

In one or more particular embodiments, the present disclosure is directed to N-cyclohexyl-3-((3,4-dichlorophenethyl)amino)-N-(2-((2-hydroxy-2-(3-oxo-3,4-dihydro-2H-benzo[b][1,4]oxazin-8-yl)ethyl)amino)ethyl)propanamide, or a pharmaceutically acceptable salt thereof.

In yet another particular embodiment, the present disclosure is directed to a method of treating cancer comprising administering a therapeutically effective dosage of a compound of Formula (I), or a pharmaceutically acceptable salt thereof, to a person in need thereof.

In yet another particular embodiment, the present disclosure is directed to a formulation comprising a compound of Formula (I), or a pharmaceutically acceptable salt thereof, and one or more pharmaceutically acceptable excipients.

Other objects and features will be in part apparent and in part pointed out hereinafter.

DETAILED DESCRIPTION OF THE DISCLOSURE

As further detailed herein below, the present disclosure is generally directed to compounds, and pharmaceutically acceptable salts thereof, that may inhibit the activity of human SMYD2, and more particularly to such compounds and salts that have cellular anti-proliferative activities by the inhibition of SMYD2 protein lysine methyltransferase. As a result, the compounds and salts of the present disclosure may advantageously be used as part of a therapy associated with tumor suppression, including for example the treatment of various types of cancer. The present disclosure is still further directed to pharmaceutical compositions comprising such compounds or salts, and methods of treatment wherein the compositions are administered, as further detailed herein below.

Notably, the compounds of the present disclosure include structural modifications over known compounds, including for example those disclosed in WO 2008/075025 (the entire contents of which are incorporated herein by reference for all relevant and consistent purposes), in order to modify and/or improve their performance in some way.

A. Compounds and Related Salts

Accordingly, the present disclosure is directed to a compound of Formula (I):

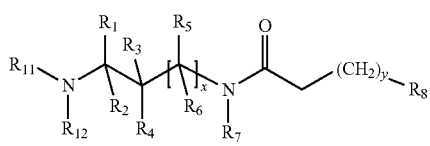

or a pharmaceutically acceptable salt thereof, wherein:

each of $R_1$, $R_2$, $R_3$, $R_4$, $R_5$, and $R_6$ are independently hydrogen or $C_{1-6}$ alkyl;

x has a value from 0 to 1;

y has a value from 0 to 3;

$R_7$ is a $C_4$-$C_6$ cycloalkyl;

$R_8$ is —$OR_9$ or —$NHR_{10}$;

$R_9$ is a $C_{1-10}$ alkyl;

$R_{10}$ is a $C_{1-2}$ alkyl substituted with a phenyl, wherein the phenyl is optionally further substituted with halogen; and, (i) $R_{11}$ and $R_{12}$ are taken together with the nitrogen atom to which they are bound to form a 4-6 member, optionally substituted heterocyclic ring: or alternatively, (ii) one of $R_{11}$ and $R_{12}$ is hydrogen, and the other is selected from:

(a) a pyrazolopyrimidinyl ring having a structure:

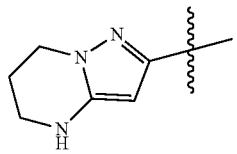 [SMILES: *c1cc2n(n1)CCCN2]

and being optionally substituted with one or more $C_{1-5}$ alkyl substituents; and, (b) a $C_{1-3}$ substituted alkyl or $C_{1-3}$ substituted hydroxyalkyl, wherein said substituent is selected from the group consisting of piperidinyl, pyrrolidinyl, cyanophenyl, and a moiety having a structure:

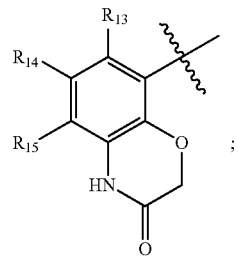

wherein $R_{13}$, $R_{14}$, and $R_{15}$ are each independently selected from hydrogen, halogen, hydroxyl, trifluoromethyl, cyano, carboxyl, $C_{1-6}$ alkyl, $C_{1-6}$ alkoxy, and $C_{1-6}$ alkylcarbonyl; provided that if one of $R_{11}$ and $R_{12}$ is $C_{1-3}$ substituted alkyl and $R_{15}$ is hydroxyl, then $R_7$ comprises a $C_4$ or $C_5$ unsubstituted cycloalkyl, or $R_8$ is —$OR_9$, or $R_8$ is —$NHR_{10}$, wherein $R_{15}$ is methyl substituted with a phenyl, optionally further substituted with a halogen.

In the context of the present disclosure, unless otherwise stated, an alkyl substituent group or an alkyl moiety in a substituent group may be linear or branched. Examples of $C_{1-6}$ alkyl groups/moieties include methyl, ethyl, n-propyl, isopropyl, n-butyl, iso-butyl, tert-butyl, n-pentyl, n-hexyl, etc.

In the context of the present disclosure, unless otherwise stated, an alkoxy substituent group or an alkoxy moiety in a substituent group may be linear or branched. Examples of $C_{1-6}$ alkoxy groups/moieties include methoxy, ethoxy, n-propoxy, isopropoxy, n-butoxy, iso-butoxy, tert-butoxy, n-pentoxy, n-hexoxy, etc.

In the context of the present disclosure, unless otherwise stated, a hydroxyalkyl substituent group or a hydroxyalkyl moiety in a substituent group may be linear or branched. Examples of $C_{1-6}$ hydroxyalkyl groups/moieties include methyl, ethyl, n-propyl, isopropyl, n-butyl, iso-butyl, tert-butyl, n-pentyl, n-hexyl, etc., each of which comprises at least one hydroxyl group substituent in place of a hydrogen.

In the context of the present disclosure, halogen encompasses fluoro, chloro, bromo, and iodo substituents, and in one particular embodiment refers to a chloro substituent.

In the context of the present disclosure, cycloalkyl is a non-aromatic ring that can comprise one, two or three non-aromatic rings, and is, optionally, fused to a benzene ring (for example to form an indanyl, or 1,2,3,4-tetrahydronaphthyl ring). Examples of cycloalkyl include cyclopropyl, cycobutyl, cyclopentyl, cyclohexyl, cycloheptyl, cyclooctyl, bicyclo[2.2.1]heptyl, cyclopentenyl, cyclohexenyl or adamantyl.

In the context of the present disclosure, heterocyclic ring is an aromatic or non-aromatic ring having from three to eight total atoms forming the ring system. The atoms within the ring system comprise carbon and at least one of nitrogen, sulfur, and oxygen. A heterocyclic ring may be fused to a homocyclic ring or another heterocyclic ring. The fused ring system may be aromatic or non-aromatic. Examples include aziridine, azirine, oxirane, oxirene, thirane, thiirene, azetidine, azete, oxetane, oxete, thietane, thiete, diazetidine, dioxetane, dioxete, dithietane, dithiete, pyrrolidine, pyrrole, tetrahydrofuran, furan, thiolane, thiophene, imidazolidine, imidazole, pyrazolidine, pyrazole, oxasolidine, oxazole, isoxazolidine, isoxazole, piperidine, pyridine, oxane, pyran, thiane, thiopyran, piperazine, diazines, morpholine, oxazine, etc.

In a particular embodiment, each of $R_1$, $R_2$, $R_3$, $R_4$, and if present, $R_5$ and $R_6$ are independently hydrogen. Additionally, x has a value of 0, and/or y has a value of 1.

Additionally or alternatively, $R_8$ is —$OR_9$, wherein $R_9$ is methyl, ethyl, n-propyl, or isopropyl. In a particular embodiment, $R_9$ is preferably methyl.

Alternative, $R_8$ is —$NHR_{10}$, wherein $R_{19}$ is a $C_{1-2}$ alkyl substituted with a phenyl ring, the phenyl ring being optionally further substituted with one or more halogens, such as chloro or bromo. In a particular embodiment, the phenyl ring is not further substituted. In another particular embodiment, the phenyl ring is di-halo substituted, each halogen substituent being for example bound to adjacent carbon atoms on the phenyl ring. More particularly, $R_8$ may be —$NHR_{10}$, wherein $R_{10}$ is a $C_{1-2}$ alkyl substituted with a dichloro-substituted phenyl having the structure:

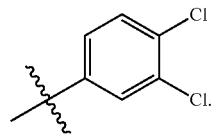 [SMILES: *c1ccc(Cl)c(Cl)c1]

Additionally or alternatively, $R_{11}$ and $R_{12}$ may be taken together with the nitrogen atom to which they are bound to form a heterocyclic ring, the ring having for example a structure selected from:

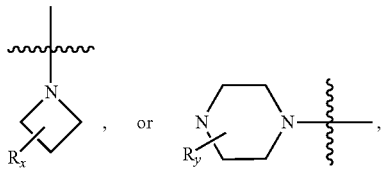

wherein R is selected from for example hydrogen and methoxypyridinyl, and $R_y$ is selected from for example hydrogen and indolinyl. More particularly, in one embodiment $R_{11}$ and $R_{12}$ are taken together with the nitrogen atom to which they are bound to form a heterocyclic ring having the structure:

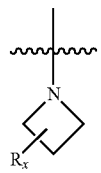

wherein $R_x$ is hydrogen, or has the following structure:

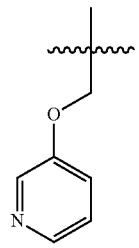

Alternatively, in another particular embodiment, $R_{11}$ and $R_{12}$ are taken together with the nitrogen atom to which they are bound to form a heterocyclic ring having a structure:

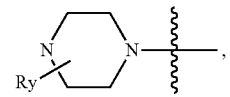

wherein $R_y$ hydrogen, or has following structure:

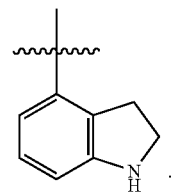 [SMILES: *c1cccc2c1CCN2]

Alternatively, one of $R_{11}$ and $R_{12}$ is hydrogen and the other comprises a pyrazolopyrimidinyl ring having a structure:

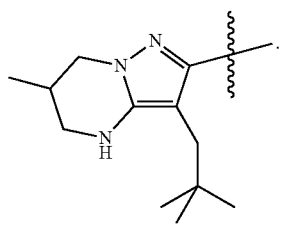 [SMILES: *c1nn2c(c1CC(C)(C)C)NCC(C)C2]

In yet another alternative embodiment, one of $R_{11}$ and $R_{12}$ is hydrogen and the other comprises a $C_{1-3}$ piperidinyl-substituted alkyl, and more particularly is a $C_3$ piperidinyl-substituted alkyl having the following structure:

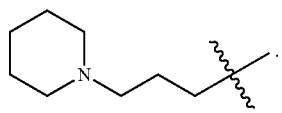 [SMILES: *CCCN1CCCCC1]

In yet another alternative embodiment, one of $R_{11}$ and $R_{12}$ is hydrogen and the other comprises a $C_{1-3}$ pyrrolidinyl-substituted alkyl, and more particularly is a $C_2$ pyrrolidinyl-substituted alkyl have the following structure:

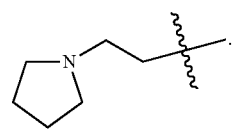 [SMILES: *CCN1CCCC1]

In yet another alternative embodiment, one of $R_{11}$ and $R_{12}$ is hydrogen and the other comprises a $C_{1-3}$ cyanophenyl-substituted alkyl, and more particularly comprises the following structure:

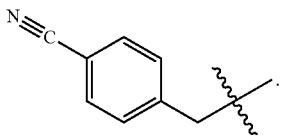 [SMILES: *Cc1ccc(C#N)cc1]

In yet another alternative embodiment, one of $R_{11}$ and $R_{12}$ is hydrogen and the other comprises a $C_{1-3}$ methylindolizinyl-substituted alkyl, and more particularly comprises the following structure:

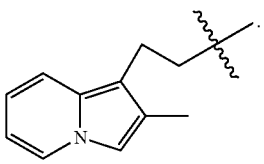 [SMILES: *CCc1c(C)cn2ccccc12]

In yet another alternative embodiment, one of $R_{11}$ and $R_{12}$ is hydrogen and the other comprises a $C_{1-3}$ substituted alkyl, and more particularly a substituted ethyl, comprising a substituent having the structure:

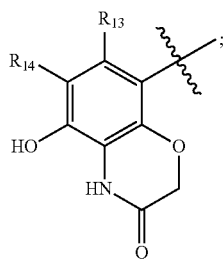

wherein $R_{13}$ and $R_{14}$ are as previously defined above, and more particularly are hydrogen; and, $R_7$ comprises a $C_4$ or $C_5$ unsubstituted cycloalkyl, In yet another alternative embodiment, one of $R_{11}$ and $R_{12}$ is hydrogen and the other comprises a $C_{1-3}$ substituted alkyl, and more particularly a substituted ethyl, comprising a substituent having the structure:

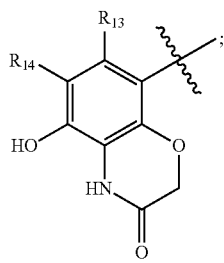

wherein $R_{13}$ and $R_{14}$ are as previously defined above, and more particularly are hydrogen; and, $R_8$ is —$OR_9$, wherein $R_9$ is defined as above, and more particularly is selected from methyl, ethyl, n-propyl, and isopropyl, and still more particularly is methyl.

In yet another alternative embodiment, one of $R_{11}$ and $R_{12}$ is hydrogen and the other comprises a $C_{1-3}$ substituted alkyl, and more particularly a substituted ethyl, comprising a substituent having the structure:

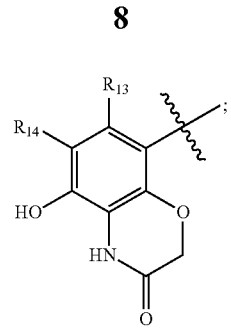

wherein $R_{13}$ and $R_{14}$ are as previously defined above, and more particularly are hydrogen; and, $R_8$ is —$NHR_{10}$, wherein $R_{10}$ is methyl substituted with a phenyl, optionally further substituted with a halogen. In one particular embodiment, $R_{10}$ is methyl or ethyl, which is substituted with an optionally substituted phenyl. In another embodiment, the phenyl is unsubstituted. In another embodiment, the phenyl is a chloro-substituted phenyl having the structure:

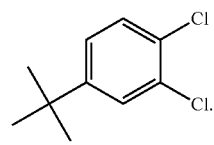

In yet another alternative embodiment, one of $R_{11}$ and $R_{12}$ is hydrogen and the other comprises a $C_{1-3}$ substituted hydroxyalkyl comprising a substituent having the structure:

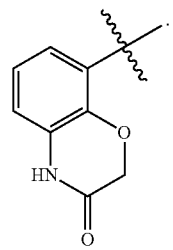 [SMILES: *c1cccc2c1OCC(=O)N2]

In another embodiment, $R_8$ is —$NHR_{10}$, wherein $R_{10}$ is defined as above. In another embodiment, $R_{10}$ is methyl or ethyl, which is substituted with an optionally substituted phenyl. In another embodiment, the phenyl is unsubstituted. In another embodiment, the phenyl is a chloro-substituted phenyl having the structure:

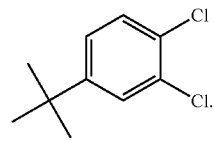

In another embodiment, one of $R_{11}$ and $R_{12}$ is hydrogen and the other comprises a substituent having the structure:

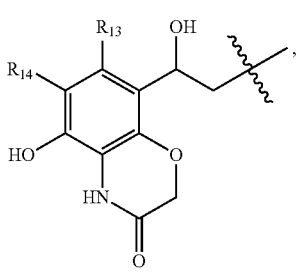

wherein $R_{13}$, $R_{14}$, and $R_{15}$ are as previously defined above, and in one particular embodiment are each hydrogen. Notably, in this embodiment, the $R_{11}$ or $R_{12}$ moiety comprises a chiral carbon atom. As shown in the examples, the enantiomers can be prepared separately. Additionally, $R_8$ may be —$NHR_{10}$, wherein $R_{10}$ is defined as above, and in particular is methyl or ethyl, which is substituted with an optionally substituted phenyl. In another particular embodiment, the phenyl is unsubstituted, or alternatively is chloro-substituted, having the structure:

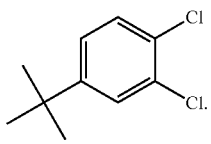

Accordingly, in particular embodiments the compound of the present disclosure may have one of the following structures:

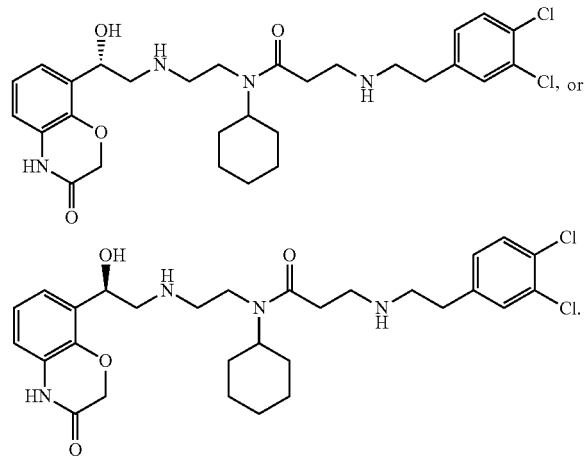

The compounds of Formula (I) may optionally exist as a pharmaceutically acceptable salt, and more particular may be an acid addition salt, a basic addition salt or a zwitterion. Salts of compounds of Formula (I) may be prepared during their isolation or following their purification. Acid addition salts are those derived from the reaction of a compound of Formula (I) with an acid. Such salts may include, for example, the acetate, adipate, alginate, ascorbate, bicarbonate, citrate, aspartate, benzoate, benzenesulfonate (besylate), bisulfate, butyrate, camphorate, camphorsufonate, cinnamate, citrate, 2,5-dichlorobenzenesulfonate, digluconate, ethanesulfonate, edisylate (ethane-1,2-disulfonate or ethane-1-(sulfonic acid)-2-sulfonate), formate, 2-furoate, 3-furoate, fumarate, glycerophosphate, glutamate, glycolate, hemisulfate, heptanoate, hexanoate, hydrochloride (for example a monohydrochloride or a dihydrochloride), hydrobromide (for example a monohydrobromide or a dihydrobromide), hydroiodide, isethionate (2-hydroxyethylsulfonate), lactobionate, lactate (e.g., L-lactate, D-lactate), malate maleate, malonate, D-mandelate, L-mandelate, mesitylenesulfonate, (e.g., 2-mesitylenesulfonate,) methanesulfonate, naphthylenesulfonate (e.g., 2-naphthalenesulfonate), napadisylate (naphthalene-1,5-disulfonate or naphthalene-1-(sulfonic acid)-5-sulfonate), nicotinate, oleate, oxalate, pamoate, pectinate, persulfate, phosphate, picrate, propionate, pyruvate, saccharinate, stearate, succinate, sulfate, tartrate (e.g., L-tartrate, D-tartrate), thiocyanate, trichloroacetic, trifluoroacetate (for example a mono-trifluoroacetate or a di-trifluoroacetate), para-toluenesulfonate, undecanoate, and xinafoate salts of the compounds of Formula (I). Basic addition salts of the compounds of Formula (I) are those derived from the reaction of such compounds with, for example, the bicarbonate, carbonate, hydroxide or phosphate of cations such as lithium, sodium, potassium, calcium and magnesium. In another aspect of the present disclosure, the stoichiometry of the salt may be, for example, a hemi-salt, or a mono- or di-salt.

Representative compounds of Formula (I) include the following:

(R)-N-cyclohexyl-3-((3,4-dichlorophenethyl)amino)-N-(2-((2-hydroxy-2-(3-oxo-3,4-dihydro-2H-benzo[b][1,4]oxazin-8-yl)ethyl)amino)ethyl)-propanamide;

(S)-N-cyclohexyl-3-((3,4-dichlorophenethyl)amino)-N-(2-((2-hydroxy-2-(3-oxo-3,4-dihydro-2H-benzo[b][1,4]oxazin-8-yl)ethyl)amino)ethyl)-propanamide;

N-cyclohexyl-3-((3,4-dichlorobenzy)amino)-N-(2-((2-(5-hydroxy-3-oxo-3,4-dihydro-2H-benzo[b][1,4]oxazin-8-yl)ethyl)amino)ethyl)propanamide;

N-cyclopentyl-N-(2-((2-(5-hydroxy-3-oxo-3,4-dihydro-2H-benzo[b][1,4]oxazin-8-yl)ethyl)amino)ethyl)-3-(phenethylamino)propanamide;

N-cyclopentyl-3-((3,4-dichlorophenethyl)amino)-N-(2-((2-(5-hydroxy-3-oxo-3,4-dihydro-2H-benzo[b][1,4]oxazin-8-yl)ethyl)amino)ethyl)propanamide;

N-cyclohexyl-3-((3,4-dichlorophenethyl)amino)-N-(2-((3-(piperidin-1-yl)propyl)amino)ethyl)propanamide;

N-cyclohexyl-3-((3,4-dichlor)phenethyl)amino)-N-(2-((2-(pyrrolidin-1-yl)ethyl)amino)ethyl)propanamide;

N-(2-((4-cyanobenzyl)amino)ethyl)-N-cyclohexy-3-((3,4-dichloro-phenethyl)amino)propanamide;

N-cyclohexyl-3-((3,4-dichlorophenethyl)amino)-N-(2-((6-methy-3-neopentyl-4,5,6,7-tetrahydropyrazolo[1,5-a]pyrimidin-2-yl)amino)ethyl)propanamide;

(S)-N-cyclohexy-3-(phenethylamino)-N-(2-(2-((pyrdin-3-yloxy)-methyl)azetidin-1-yl)ethyl)propanamide;

(R)-N-cyclohexyl-3-(phenethylamino)-N-(2-(2-((pyridin-3-yloxy)-methyl)azetidin-1-yl)ethyl)propanamide;

N-cyclohexyl-N-(2-((2-(5-hydroxy-3-oxo-3,4-dihydro-2H-benzo-[b][1,4]oxazin-8-yl)ethyl)amino)ethyl)-3-methoxypropanamide;

N-cyclohexy-3-((3,4-dichlorophenethyl)amino)-N-(2-(4-(indolin-4-yl)piperazin-1-yl)ethyl)propanamide;

N-cyclohexy-3-((3,4-dichlorophenethyl)amino)-N-(2-((3-(pyrrolidin-1-yl)propyl)amino)ethyl)propanamide;

N-cyclobutyl-N-(2-((2-(5-hydroxy-3-oxo-3,4-dihydro-2H-benzo-[b][1,4]oxazin-8-yl)ethyl)amino)ethyl)-3-(phenethylamino)propanamide;

N-cyclobutyl-3-((3,4-dichlorophenethyl)amino)-N-(2-((2-(5-hydroxy-3-oxo-3,4-dihydro-2H-benzo[b][1,4]oxazin-8-yl)ethyl)amino)ethyl)propanamide;

N-cyclohexyl-3-((2,3-dichlorophenethyl)amino)-N-(2-((2-(2-methyl-indolizin-1-yl)ethyl)amino)ethyl)propanamide;

and pharmaceutically acceptable salts of one or more of the above-noted compounds.

In another particular embodiment, the compound is N-cyclohexyl-3-((3,4-dichlorophenethyl)amino)-N-(2-((2-hydroxy-2-((3-oxo-3,4-dihydro-2H-benzo-[b][1,4]oxazin-8-yl)ethyl)amino)ethyl)propanamide, in either the racemic, (R) or (S) stereochemical form, or a pharmaceutically acceptable salt thereof.

The synthesis of these representative compounds of Formula (I) is provided in the Examples that follow.

B. Methods of Use and Treatment

In another embodiment of the present disclosure, the compounds of Formula (I) and their pharmaceutically acceptable salts may be used in the treatment of cancers including, for example: mesothioloma, bladder cancer, pancreatic cancer, skin cancer, cancer of the head or neck, cutaneous or intraocular melanoma, ovarian cancer, breast cancer, uterine cancer, carcinoma of the fallopian tubes, carcinoma of the endometrium, carcinoma of the cervix, carcinoma of the vagina, carcinoma of the vulva, bone cancer, bone marrow cancer, ovarian cancer, cervical cancer, colon cancer, rectal cancer, cancer of the anal region, stomach cancer, gastrointestinal (gastric, colorectal, and duodenal) cancer, chronic lymphocytic leukemia, esophageal cancer, esophageal squamous cell carcinoma, cancer of the small intestine, cancer of the endocrine system, cancer of the thyroid gland, cancer of the parathyroid gland, cancer of the adrenal gland, sarcoma of soft tissue, cancer of the urethra, cancer of the penis, testicular cancer, hepatocellular cancer (hepatic and billiary duct), primary or secondary central nervous system tumor, brain cancer, primary or secondary brain tumor, Hodgkin's disease, chronic or acute leukemia, chronic myeloid leukemia, lymphocytic lymphomas, lymphoblastic leukemia, follicular lymphoma, lymphoid malignancies of T-cell or B-cell origin, melanoma, myelogenous leukemia, multiple myeloma, oral cancer, ovarian cancer, non-small cell lung cancer, prostate cancer, small cell lung cancer, cancer of the kidney and ureter, spleen cancer, renal cell carcinoma, carcinoma of the renal pelvis, neoplasms of the central nervous system, primary central nervous system lymphoma, non-Hodgkin's lymphoma, spinal axis tumors, brains stem glioma, pituitary adenoma, adrenocortical cancer, gall bladder cancer, cancer of the spleen, cholangiocarcinoma, fibrosarcoma, neuroblastoma, retinoblasitoma, or a combination thereof.

In still another embodiment of the present disclosure, the present disclosure is directed to methods of treating one of the above-noted cancers, or a combination thereof, in a patient, said methods comprising administering thereto a therapeutically effective amount of one or more of the compounds of Formula (I).

In still another embodiment, the present disclosure is directed to compositions for treating one of the above-noted cancers, or a combination thereof, said compositions comprising an excipient and a therapeutically effective amount of one or more compounds of Formula (I).

In this regard it is to be noted that the present disclosure provides a compound of Formula (I), or a pharmaceutically acceptable salt thereof, as hereinbefore defined for use in therapy. In the context of the present disclosure, the term "therapy" also includes "prophylaxis," unless there are specific indications to the contrary. The terms "therapeutic" and "therapeutically" should be construed accordingly. Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

C. Compositions, Dosages and Administration

For the above-mentioned therapeutic uses, the dosage administered will vary with the compound employed, the mode of administration, the treatment desired and/or the disorder indicated. For example, the daily dosage of the compound of the present disclosure, if inhaled, may be in the range from 0.05 micrograms per kilogram body weight (μg/kg) to 100 micrograms per kilogram body weight (μg/kg). Alternatively, if the compound is administered orally, then the daily dosage of the compound of the invention may be in the range from 0.01 micrograms per kilogram body weight (μg/kg) to 100 milligrams per kilogram body weight (mg/kg).

Compounds of Formula (I) may be administered, for example, bucally, ophthalmically, orally, osmotically, parenterally (intramuscularly, intraperintoneally intrasternally, intravenously, subcutaneously), rectally, topically, transdermally, vaginally and intraarterially as well as by intraarticular injection, infusion, and placement in the body, such as, for example, the vasculature by means of, for example, a stent.

The compounds of Formula (I) and pharmaceutically acceptable salts thereof may be used on their own, or alternatively may be administered in the form of a pharmaceutical composition in which the Formula (I) compound, or salt thereof, is in association with a pharmaceutically acceptable excipient, adjuvant, diluent or carrier. Suitable excipients include, but are not limited to, encapsulators and additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents, mixtures thereof and the like. Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The pharmaceutical compositions may be administered topically (e.g. to the skin or to the lung and/or airways) in the form, e.g., of creams, solutions, suspensions, heptafluoroalkane (HFA) aerosols and dry powder formulations, for example, formulations in an inhaler device; or systemically, e.g. by oral administration in the form of tablets, capsules, syrups, powders or granules; or by parenteral administration in the form of solutions or suspensions; or by subcutaneous administration; or by rectal administration in the form of suppositories; or transdermally.

Dry powder formulations and pressurized HFA aerosols of the compounds of the invention may be administered by oral or nasal inhalation. For inhalation, the compound is desirably finely divided. The finely divided compound preferably has a mass median diameter of less than 10 μm, and may be suspended in a propellant mixture with the assistance of a dispersant, such as a $C_{8-20}$ fatty acid or salt thereof, (for example, oleic acid), a bile salt, a phospholipid, an alkyl saccharide, a perfluorinated or polyethoxylated surfactant, or other pharmaceutically acceptable dispersant. The compounds of the invention may also be administered by means of a dry powder inhaler. The inhaler may be a single or a multi dose inhaler, and may be a breath actuated dry powder inhaler. Another possibility is to process the finely divided powder into spheres which break up during the inhalation procedure. This spheronized powder may be filled into the drug reservoir of a multidose inhaler, for example, that known as the Turbuhaler® in which a dosing unit meters the desired dose which is then inhaled by the patient. With this system the active ingredient, with or without a carrier substance, is delivered to the patient.

For oral administration the compound of the invention may be admixed with an adjuvant or a carrier. Carrier forms include coated and uncoated tablets, soft gelatin capsules, and hard gelatin capsules. Carriers for preparation of compositions comprising a compound having formula (I) to be administered orally include, but are not limited to, agar, alginic acid, aluminum hydroxide, benzyl alcohol, benzyl benzoate, 1,3-butylene glycol, calcium stearate, carbomers, castor oil, cellulose, cellulose acetate, cocoa butter, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl celluose, isopropanol, isotonic saline, lactose, magnesium hydroxide, magnesium stearate, malt, mannitol, monoglycerides, olive oil, paraffin, peanut oil, polyethylene glycol, potassium phosphate salts, potato starch, povidone, propylene glycol, Ringer's solution, saccharose, safflower oil, sesame oil, sodium carboxymethyl cellulose, sodium phosphate salts, sodium lauryl sulfate, sodium sorbitol, soybean oil, a starch, for example, potato starch, corn starch or amylopectin, stearic acids, stearyl fumarate, sucrose, surfactants, talc, tragacanth, tetrahydrofurfuryl alcohol, vegetable oils and triglycerides, as wax, water, mixtures thereof and the like. Excipients for preparation of compositions comprising a compound having formula (I) to be administered ophthalmically or orally include, but are not limited to, 1,3-butylene glycol, castor oil, corn oil, cottonseed oil, ethanol, fatty acid esters of sorbitan, germ oil, groundnut oil, glycerol, isopropanol, olive oil, polyethylene glycols, propylene glycol, sesame oil, water, mixtures thereof and the like. Excipients for preparation of compositions comprising a compound having formula (I) to be administered osmotically include, but are not limited to, chlorofluorohydrocarbons, ethanol, water, mixtures thereof and the like. Excipients for preparation of compositions comprising a compound having formula (I) to be administered parenterally include, but are not limited to, 1,3-butanediol, castor oil, corn oil, cottonseed oil, dextrose, germ oil, groundnut oil, liposomes, oleic acid, olive oil, peanut oil. Ringers solution, safflower oil, sesame oil, soybean oil, U.S.P. or isotonic sodium chloride solution, water, mixtures thereof and the like. Excipients for preparation of compositions comprising a compound having formula (I) to be administered rectally or vaginally include, but are not limited to, cocoa butter, polyethylene glycol, wax, mixtures thereof and the like.

Liquid preparations for oral application may be in the form of syrups or suspensions, for example, solutions containing the compound of the invention, the balance being sugar and a mixture of ethanol, water, glycerol and propylene glycol. Optionally such liquid preparations may contain coloring agents, flavoring agents, saccharine and/or carboxymethylcellulose as a thickening agent or other excipients known in the art.

D. Assays—Binding Affinity

Binding affinity of compounds having formula (I) to SMYD2 is indicia of their inhibition of the activity of this protein lysine methyltransferase. To determine the binding affinity of representative compounds having formula (I) to SMYD2, example compounds having Formula (I) were diluted in assay buffer (as detailed below) to concentrations of 0.0008 micromolar, 0.002 micromolar, 0.007 micromolar, 0.02 micromolar, 0.07 micromolar, 0.2 micromolar, 0.6 micromolar, 1.9 micromolar, 5 micromolar, 17.5 micromolar, and 50 micromolar and added (Echo Liquid Handler by Labcyte) to the wells of an assay plate (PerkinElmer Proxy Plate-384, Cat #6008289). 5 microliters of a 2×SMYD2 enzyme solution (20 nM, 1.8 mg/mL in assay buffer) were added to each well. To the control wells was also added 5 microliters of assay buffer. The assay buffer was comprised of Tris Cl (50 mMolar, obtained from Sigma, Cat # T23139 1 L), Tween 20 (0.01%, obtained from BioRad, Cat #170-6531), BSA (0.005%, obtained from Sigma, Cat# A-3059-50G), and DTT (1 mM, dithiothreitol (DTT)). The wells were incubated at room temperature for 30 minutes. The reaction was initiated by adding 2×p53 peptide (2.5 micromolar, GenMed, Cat #62529)+SAM (2 micromolar, S-adenosyl methionine, AK Scientific).

Into the wells of the counter screen plate was added 5 microliters 2×SAH (300 nM, S-adenosyl homocysteine (SAH)), except the control wells. The counter screen plates are run to ensure that any compound activity observed are not artifacts. To the control wells was added 5 microliters of assay buffer, which comprised Tris Cl (50 mMolar, obtained from Sigma, Cat # T23139 1 L), Tween 20 (0.01%, obtained from BioRad, Cat #170-6531), BSA (0.005%, obtained from Sigma, Cat# A-3059-50G), and DTT (1 mM, dithiothreitol).

Into all wells was added 5 microliters of 2×SAM. The plates were covered and incubated overnight at room temperature. 2× detection reagent was prepared comprising Tb Chelate antihomocysteine mAb (1 nanomolar, E001892-097) and Probe OG-SAH (2 nanomolar, A-1344409.2, lot #1857509), 10 microliters of 2× detection reagent was added to all wells, and the plates were incubated for four hours at room temperature. Analysis of the wells was by the Laser Lentha Low Volume Envision Protocol (emission wavelength of 520 nm; laser excitation wavelength of 337 nm). Percentage of inhibition data is provided in the following Table 1.

TABLE 1

| Example | TRFRET $IC_{50}$ (μM) |
|---|---|
| 1 (racemate) | 0.065 |
| 1a (S enantiomer) | 0.023 |
| 1b (R enantiomer) | 0.138 |
| 2 | 2.027 |
| 3 | 3.741 |
| 4 | 10.032 |
| 5 | 11.150 |
| 6 | 12.100 |
| 7 | 16.0 |
| 8 | 32.80 |
| 9 | >50 |
| 10 | >50 |
| 11 | >50 |
| 12 | 9.830 |
| 13 | 7.420 |
| 14 | >50 |

TABLE 1-continued

| Example | TRFRET IC$_{50}$ (μM) |
|---|---|
| 15 | 3.79 |
| 16 | 3.44 |

The following non-limiting examples are provided to further illustrate the present invention.

EXAMPLES

Example 1

N-cyclohexyl-3-((3,4-dichlorophenethyl)amino)-N-(2-((2-hydroxy-2-(3-oxo-3,4-dihydro-2H-benzo[b][1,4]oxazin-8-yl)ethyl)amino)ethyl)-propanamide The synthesis of the title compounds occurred by synthesizing and reacting component molecules of the compounds as set forth in the following Schemes 1-4.

(R)-8-(2-amino-1-hydroxyethyl)-2H-benzo[b][1,4]oxazin-3(4H)-one and (S)-8-(2-amino-1-hydroxyethyl)-2H-benzo[b][1,4]oxazin-3(4H)-one were synthesized according to the following Scheme 1.

SCHEME 1.

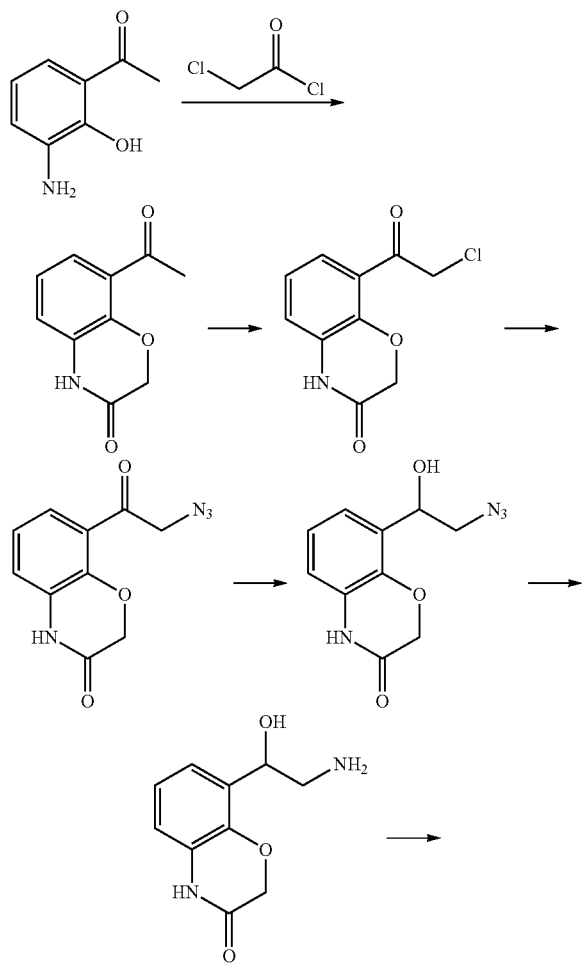

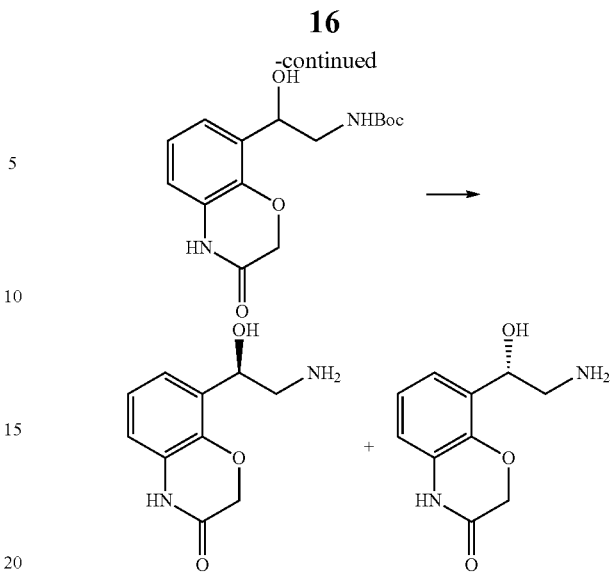

Step 1: 8-acetyl-2H-benzo[b][1,4]oxazin-3(4H)-one

To a stirred mixture of 1-(3-amino-2-hydroxyphenyl)ethanone (5.00 g, 33.1 mmol) and sodium bicarbonate (6.11 g, 72.8 mmol) in DMF (30 mL) was added 2-chloroacetyl chloride (2.89 mL, 36.4 mmol) dropwise. The mixture was stirred for 2 hours. Cesium carbonate (12.9 g, 39.7 mmol) was then added and the resulting mixture was heated at 100° C. for 20 hours. The mixture was cooled to ambient temperature, quenched with water, and then extracted with ethyl acetate. The combined organic layers were washed with water and brine, dried over anhydrous Na$_2$SO$_4$, filtered and then evaporated in vacuo. The residue was washed with ether and dried to afford the title compound. (5.80 g, 30.4 mmol, 84% yield) as a beige solid. $^1$H NMR (400 MHz, DMSO-d$_6$): δ 10.88 (s, 1H), 7.25 (dd, J$_1$=7.7 Hz, J$_2$=1.7 Hz, 1H), 7.09 (dd, J$_1$=7.7, J$_2$=1.7 Hz, 1H), 7.03 (t, J=7.7 Hz, 1H), 4.72 (s, 2H), 2.55 (s, 3H). MS (ESI) m/z 192.1 [M+H]$^+$.

Step 2: 8-(2-chloroacetyl)-2H-benzo[b][1,4]oxazin-3(4H)-one

Benzyltrimethylammonium dichloroiodate (20.0 g, 57.5 mmol) was added to a stirred solution of 8-acetyl-2H-benzo[b][1,4]oxazin-3(4H)-one (5.00 g, 26.2 mmol) in dichloromethane (100 mL), AcOH (33 mL) and water (5.5 mL). The resultant mixture was stirred at 65° C. for 20 hours. It was then cooled to ambient temperature, quenched via addition of an aqueous NaHSO$_3$ solution (5.78 g in 100 mL) and stirred further for 30 minutes. The mixture then was diluted with Et$_2$O (200 mL) and the resulting solid was collected with filtration, washed with water, extracted with diethyl ether, concentrated, and dried under vacuum at 40° C. to afford the title compound. (5.30 g, 23.5 mmol, 90% yield) as a light brown solid. $^1$H NMR (400 MHz, DMSO-d$_6$): δ 10.93 (s, 1H), 7.37 (dd, J=7.7, 1.7 Hz, 1H), 7.14 (dd, J=7.7, 1.7 Hz, 1H), 7.08 (t, J=7.7 Hz, 1H), 5.02 (s, 2H), 4.73 (s, 2H). MS (ESI) m/z 226.1 [M+H]$^+$.

Step 3: 8-(2-azidoacetyl)-2H-benzo[b][1,4]oxazin-3(4H)-one

To a suspension of 8-(2-chloroacetyl)-2H-benzo[b][1,4]oxazin-3(4H)-one (4.00 g, 17.7 mmol) in DMF (50 mL) was carefully added sodium azide (1.44 g, 22.2 mmol). After addition, the resulting mixture was stirred for 2 hours and then poured onto ice/water. The precipitated product was collected with filtration, washed with water and then dried in vacuo at 40° C. to afford the title compound (4.00 g, 17.2 mmol, 97% yield) as a light brown solid. $^1$H NMR (400 MHz, DMSO-d$_6$) δ 10.93 (s, 1H), 7.42 (dd, J$_1$=7.7, J$_2$=1.6 Hz, 1H), 7.14 (dd, J$_1$=7.6, J$_2$=1.5 Hz, 1H), 7.09 (t, J=7.7 Hz, 1H), 4.71 (d, J=11.4 Hz, 4H). MS (ESI) m/z 233.1 [m+H]$^+$.

Step 4: 8-(2-amino-1-hydroxyethyl)-2H-benzo[b][1,4]oxazin-3(4H)-one

A suspension 8-(2-azidoacetyl)-2H-benzo[b][1,4]oxazin-3(4H)-one (10 g, 43.1 mmol) in a mixture of MeOH (60 mL) and THF (60 mL) was treated with sodium borohydride (2.49 g, 65.9 mmol), and the resultant mixture was stirred at room temperature for 2 hours. The mixture was partitioned between EtOAc and brine. The organic layer was then separated, dried, filtered and concentrated in vacuo. The residue was triturated with acetone (20 mL) to yield 11 g of intermediate, of which 7 g was re-dissolved into ethanol (150 mL). To this was added Pd/C (10%, 89% wet, 700 mg). The resulting mixture was briefly evacuated and then back-filled with hydrogen. This operation was repeated three times. The resulting mixture was then stirred under a hydrogen atmosphere (balloon pressure) at room temperature for 12 hours. The catalyst was removed by filtration and the filtrate was concentrated in vacuo. The residue was washed with ether and then dried to give the title compound (6.0 g, 85% purity, 24.4 mmol, 89% yield over two steps) as a white solid. MS (ESI) m/z 209.2 [M+H]$^+$.

Step 5: tert-Butyl 2-hydroxy-2-(3-oxo-3,4-dihydro-2H-benzo[b][1,4]oxazin-8-yl)ethylcarbamate To a solution of 8-(2-amino-1-hydroxyethyl)-2H-benzo[b][1,4]oxazin-3(4H)-one (7.0 g, 33.6 mmol) in DMF (150 mL) was added DMAP (0.41 g, 3.36 mmol), followed by di-tert-butyl dicarbonate (8.07 g, 37.0 mmol). The reaction mixture was stirred at room temperature for 2 hours and then quenched with a saturated aqueous NH$_4$Cl solution (about 50 mL). The aqueous layer was extracted with dichloromethane (300 mL×2). The combined organic layers were dried over sodium sulfate, filtered, and then concentrated under reduced pressure. The product was purified by silica gel chromatography (EtOAc/hexanes=1/2) to give the title compound (9.0 g, 29.2 mmol, 87% yield) as white solid. $^1$H NMR (400 MHz, CDCl$_3$) δ 9.48 (s, 1H), 7.06 (d, J=7.6 Hz, 1H), 6.87 (t, J=7.8 Hz, 1H), 6.71 (d, J=7.5 Hz, 1H), 4.99 (dd, J$_1$=17.5, J$_2$ 14.1 Hz, 2H), 4.48 (d, J=6.5 Hz, 2H), 3.40 (s, 2H), 3.26 (s, 1H), 1.35 (s, 9H). MS (ESI) m/z 235.1 [M+H]$^+$.

Step 6: (R)-8-(2-amino-1-hydroxyethyl)-2H-benzo[b][1,4]oxazin-3(4H)-one and (S)-8-(2-amino-1-hydroxyethyl)-2H-benzo[b][1,4]oxazin-3(4H)-one tert-Butyl 2-hydroxy-2-(3-oxo-3,4-dihydro-2H-benzo[b][1,4]oxazin-8-yl)ethylcarbamate (2.0 g, 6.49 mmol) was dissolved in HCl/dioxane (2 M, 10 mL, 20 mmol), and the mixture was stirred at room temperature for 12 hours. The solvent was then removed by evaporation. The residual material was treated with EtOAc (10 mL) and ether (70 mL), and the formed slurry was stirred for 30 minutes. The solid was collected by filtration, washed with ether, and then dried under reduced pressure at 40° C. to give 8-(2-amino-1-hydroxyethyl)-2H-benzol[b][1,4]oxazin-3(4H)-one hydrochloride (1.30 g, 5.31 mmol, 82% yield). After chiral separation, (R)-8-(2-amino-1-hydroxyethyl)-2H-benzo[b][1,4]oxazin-3(4H)-one and (S)-8-(2-amino-1-hydroxyethyl)-2H-benzo[b][1,4]oxazin-3(4H)-one were obtained, ee % >99% for each. $^1$H NMR (400 MHz, DMSO-d$_6$) δ 10.80 (s, 1H), 8.14 (s, 3H), 7.10 (d, J=6.8 Hz, 1H), 6.98 (t, J=7.7 Hz, 1H), 6.88 (dd, J$_1$=7.7, J$_2$=1.3 Hz, 1H), 5.98 (s, 1H), 5.07 (dd, J$_1$=9.5, J$_2$=2.3 Hz, 1H), 4.61 (q, J=15.1 Hz, 2H), 2.99 (d, J=6.6 Hz, 1H), 2.83-2.62 (m, 1H). MS (ESI) m/z 209.1 [M+H]$^+$.

Benzyl 3-(cyclohexyl(2-oxoethyl)amino)-3-oxopropyl(3,4-dichlorophenethyl)carbamate was synthesized according to the following Scheme 2.

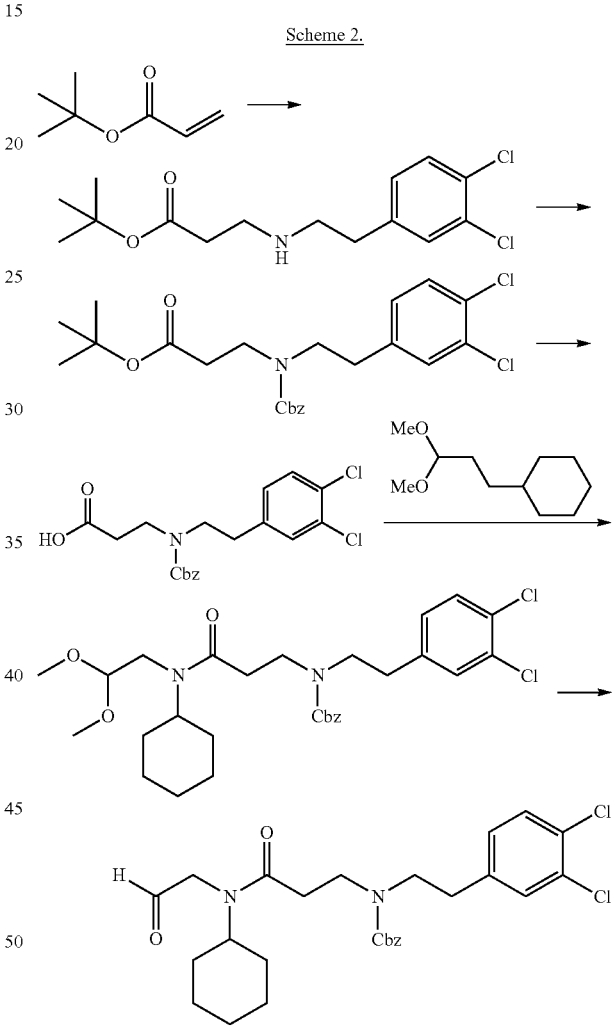

Scheme 2.

Step 1: tert-Butyl 3-(3,4-dichlorophenethylamino)propanoate

A mixture of tert-butyl acrylate (21.92 g, 171 mmol), dichlorophenyl)ethanamine (25 g, 132 mmol) in EtOH (250 mL) was stirred at room temperature overnight. The progress of the reaction was monitored by LC/MS. The mixture was then concentrated under reduced pressure, to furnish tert-butyl 3-((3,4-dichlorophenethyl)amino)propanoate (38.6 g, 112 mmol, 85% yield) as the residue, which was used in the next step without further purification. MS (ESI) m/z 320 [M+H]$^+$.

Step 2: tert-Butyl 3-benzyloxycarbonyl)(3,4-dichlorophenethyl)-amino)propanoate Benzyl chloroformate (23.00 g, 135 mmol) was added to a mixture of tert-butyl 3-(3,4-dichlorophenethylamino)propanoate (39 g, 123 mmol) and Et₃N (34.2 ml, 245 mmol) in DCM (300 mL), then the mixture was stirred overnight. The progress of the reaction was monitored by LC/MS. Ice-water (200 mL) was added to the reaction and the mixture was extracted twice with dichloromethane (500 mL×2). The combined organic phase was washed with brine, dried over magnesium sulfate, filtered, and concentrated under reduced pressure to give the residue. This was then purified by column chromatography on silica gel by using (DCM/petroleum ether=2:1) to give the title compound (43 g, 67.5 mmol, 71.0% yield). MS (ESI) m/z 476.1 [M+Na]⁺.

Step 3: 3-((Benzyloxycarbonyl)(3,4-dichlorophenethyl)-amino)propanoic acid

To the solution of tert-butyl 3-((benzyloxycarbonyl)(3,4-dichlorophenethyl)amino) propanoate (30.0 g, 66.3 mmol) in dichloromethane (50 mL) was added TFA (50 mL) dropwise. The reaction was stirred at room temperature for 3 h. The progress of the reaction was monitored by LCMS and TLC. The reaction was concentrated under reduced pressure to give the crude product. Water (50 mL) was then added and extracted twice with ethyl acetate (150 mL×2). The combined organic solvent was washed by water (50 mL×2) and dried over Na₂SO₄. After the removal of the solvent, the title compound was isolated as the residue (23.5 g, 53.4 mmol, 80% yield) and used without further purification, MS (ESI) m/z 397 [M+H]⁺.

Step 4: Benzyl 3-(cyclohexyl(2,2-dimethoxyethyl)amino)-3-oxopropyl(3,4-dichlorophenethyl)carbamate A mixture of 3-((benzyloxycarbonyl)(3,4-dichlorophenethyl)-amino)propanoic acid (38 g, 96 mmol), HOST (16.15 g, 105 mmol) and di-isopropylethylamine (36.8 ml, 211 mmol) in DMF (100 mL) was stirred at room temperature for 40 min. To this was added N-(2,2-dimethoxyethyl) cyclohexanamine (25.1 g, 134 mmol) and 1-ethyl-3-(3-dimethylaminopropyl)carbodiimide (20.22 g, 105 mmol). The reaction then was stirred at room temperature overnight. The progress of the reaction was monitored by LC/MS. Next, ice-water (150 mL) was added and stirred for 30 minutes. The mixture was extracted three times with dichloromethane (300 mL×2). The combined organic phase was washed by 1N HCl (100 mL) and a saturated solution of sodium bicarbonate (150 mL), respectively. The organic layer was dried over Na₂SO₄, filtered, and concentrated under reduced pressure to give the crude product. The residue was purified by column chromatography on silica gel using a solvent gradient of pet. ether/ethyl acetate from 5/1 to 2/1 to furnish the title compound (33 g, 58.4 mmol, 60.9% yield) as pale yellow oil. MS (ESI): m/z 567 [M+H]⁺.

Step 5: Benzyl 3-(cyclohexyl(2-oxoethyl)amino)-3-oxopropyl(3,4-dichlorophenethyl)carbamate To a solution of benzyl 3-(cyclohexyl(2,2-dimethoxyethyl)amino)-3-oxopropyl(3,4-dichlorophenethyl)carbamate (15 g, 26.5 mmol) in dichloromethane (50 mL) was added para-toluene sulfonic acid monohydrate (15.14 g, 80 mmol). The reaction was then stirred at room temperature overnight. The progress of the reaction was monitored by LC/MS. A saturated solution of NaHCO₃ was then added to adjust to a pH=8. The reaction was extracted three times with dichloromethane (150 mL×3). The combined organic layers were washed with brine, dried over magnesium sulfate and concentrated in vacuo to furnish the title compound (13 g, 22.27 mmol, 84% yield), which was used without further purification. MS (ESI): m/z 521 [M+H]⁺.

Example 1a (S)-N-cyclohexyl-3-((3,4-dichlorophenethyl)amino)-N-(2-((2-hydroxy-2-(3-oxo-3,4-dihydro-2H-benzo[b][1,4]oxazin-8-yl)ethyl)amino)-ethyl)-propanamide (S)-N-cyclohexyl-3-(3,4-dichlorophenethylamino)-N-(2-(2-hydroxy-2-(3-oxo-3,4-dihydro-2H-benzo[b][1,4]oxazin-8-yl)ethylamino)ethyl)propanamide was synthesized according to the following Scheme 3.

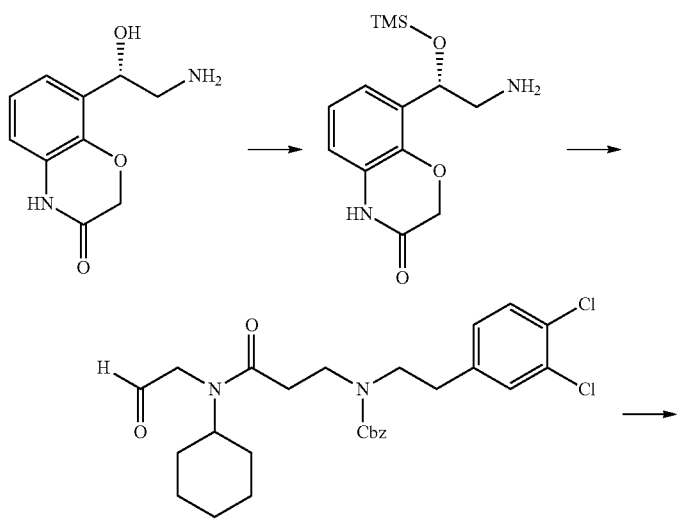

Scheme 3.

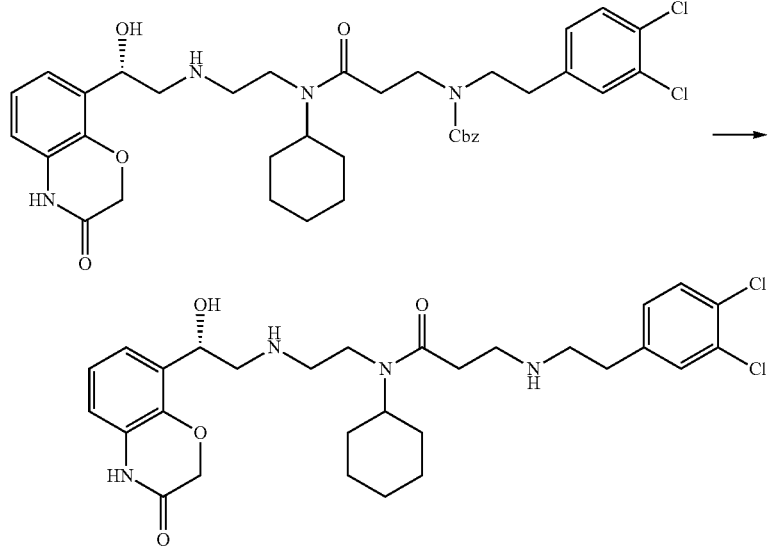

Step 1: (S)-8-(2-amino-1-(trimethylsilyloxy)ethyl)-2H-benzo[b][1,4]oxazin-3(4H)-one To a solution of (S)-8-(2-amino-1-hydroxyethyl)-2H-benzo-[b][1,4]oxazin-3(4H)-one (3.5 g, 14.30 mmol) in DMF (40 mL) was added di-isopropylethylamine (5.50 ml, 31.5 mmol) and trimethylsilylchloride (1.828 ml, 14.30 mmol) dropwise at 0° C. The reaction was stirred at this temperature for 2 hours. The progress of the reaction was monitored by LC/MS. Ice-water was the added (50 mL) and the mixture was extracted twice with ethyl actetate (100 mL×2). The combined organic phases were washed with brine, dried over MgSO$_4$, filtered and concentrated under reduced pressure to give the residue (S)-8-(2-amino-1-((trimethylsilyl)-oxy)ethyl)-2H-benzo[b][1,4]oxazin-3(4H)-one (3.0 g, 10.70 mmol, 74.8% yield) which was used without further purification. MS (ESI) m/z 281 [M+H]$^+$.

Step 2: (S)-benzyl 3-(cyclohexyl(2-(2-hydroxy-2-(3-oxo-3,4-dihydro-2H-benzo[b][1,4]oxazin-8-yl)ethyl-amino)ethyl)amino)-3-oxopropyl(3,4-dichloro-phenethyl)carbamate A mixture of (S)-8-(2-amino-1-(trimethylsilyloxy)ethyl)-2H-benzo[b][1,4]oxazin-3(4H)-one (3.45 g, 12.32 mmol), benzyl(3-(cyclohexyl(2-oxoethyl)amino)-3-oxopropyl)(3,4-dichlorophenethyl)carbamate (3.2 g, 6.16 mmol) and magnesium sulfate (1.43 g, 12.32 mmol) in dichloromethane (50 mL) and acetic acid (3.53 ml, 61.6 mmol) was stirred at ambient temperature for 5 hours. To this was added sodium triacetoxyborohydride (2.61 g, 12.32 mmol) at 0° C. slowly, then the reaction was stirred at room temperature for 18 hours. The progress of the reaction was monitored by LC/MS. Ice-water (10 mL) was added, and the mixture was extracted three times with dichloromethane (100 mL×3). The combined organic phases were washed with brine, dried over magnesium sulfate, filtered, and concentrated in vacuo. The residue was purified by column chromatography using a gradient of dichloromethane/methanol from 99/1 to 10/1 ($R_f$=0.2, DCM/MeOH=10/1) to yield the title compound as a yellow solid, which was stirred in EtAOc (20 mL) for 20 minutes, then filtered to give (S)-benzyl(3-(cyclohexyl(2-((2-hydroxy-2-(3-oxo-3,4-dihydro-2H-benzo[b][1,4]ox-azin-8-yl)ethyl)amino)ethyl)amino)-3-oxopropyl)-(3,4-dichlorophenethyl)carbamate (1.6 g, 2.248 mmol, 36.5% yield) as a white solid. $^1$H NMR (400 MHz, MeOD): δ 7.31-7.21 (m, 7H), 7.11-6.88 (m, 3H), 6.78-6.76 (m, 1H), 5.04-4.92 (m, 3H), 4.49 (d, J=7.2 Hz, 2H), 3.48-3.38 (m, 7H), 2.95-2.49 (m, 8H), 1.74-1.18 (m, 10H). MS (ESI) m/z 713 [M+H]$^+$.

Step 3: (S)-N-cyclohexyl-3-(3,4-dichlorophenethyl-amino)-N-(2-(2-hydroxy-2-(3-oxo-3,4-dihydro-2H-benzo[b][1,4]oxazin-8-yl)ethylamino)-ethyl)pro-panamide To a solution of (S)-benzyl 3-(cyclohexyl(2-(2-hydroxy-2-(3-oxo-3,4-dihydro-2H-benzo[b][1,4]oxazin-8-yl)ethyl-amino)ethyl)amino)-3-oxopropyl(3,4-dichlorophenethyl) carbamate (1.5 g, 2.108 mmol) in dichloromethane (100 ml) was added tri-bromoborane (12.65 ml, 12.65 mmol) at 0° C. dropwise. The reaction was stirred for 2 hours at this temperature. The reaction was allowed to warm to room temperature and stirred for an additional 2 hours. Ice-water (30 mL) was then carefully added, and the mixture was stirred for 1 hour. This was extracted twice with dicholom-ethane (100 mL×2) and the combined organic phases were washed with brine, dried over MgSO$_4$, filtered, and concentrated under reduced pressure to give the crude product, which was purified by Prep-HPLC to give (S)-N-cyclo-hexyl-3-((3,4-dichlorophenethyl)amino)-N-(2-((2-hydroxy-2-(3-oxo-3,4-dihydro-2H-benzo[b][1,4]oxazin-8-yl)ethyl) amino)ethyl)propanamide2,2,2-trifluoroacetate (905 mg, 1.296 mmol, 61.5% yield) as white solid. $^1$H NMR (400 MHz, MeOD): δ 7.42-7.38 (m, 2H), 7.16-7.11 (m, 2H), 6.93 (t, J=8.0 Hz, 1H), 6.81-6.78 (dd, $J_1$=8.0 Hz, $J_1$=1.2 Hz, 1H), 5.20-5.16 (dd, $J_1$=10.8 Hz, J=3.6 Hz, 1H), 4.53 (t, J=20.8 Hz, 2H), 3.56-3.27 (m, 3H), 3.27-3.20 (m, 4H), 3.13-2.82 (m, 7H), 1.78-1.1.19 (m, 11H). MS (ESI) m/z 579 [M+H]$^+$.

Example 1b (R)-N-cyclohexyl-3-((3,4-dichlorophenethyl)amino)-N-(2-((2-hydroxy-2-(3-oxo-3,4-dihydro-2H-benzo[b][1,4]oxazin-8-yl)ethyl)amino)-ethyl)-propana-mide (R)-N-cyclohexyl-3-(3,4-dichlorophenethylamino)-N-(2-(2-hydroxy-2-(3-oxo-3,4-dihydro-2H-benzo[b][1,4]oxazin- 8-yl)ethylamino)ethyl)propanamide was synthesized according to the following Scheme 4.

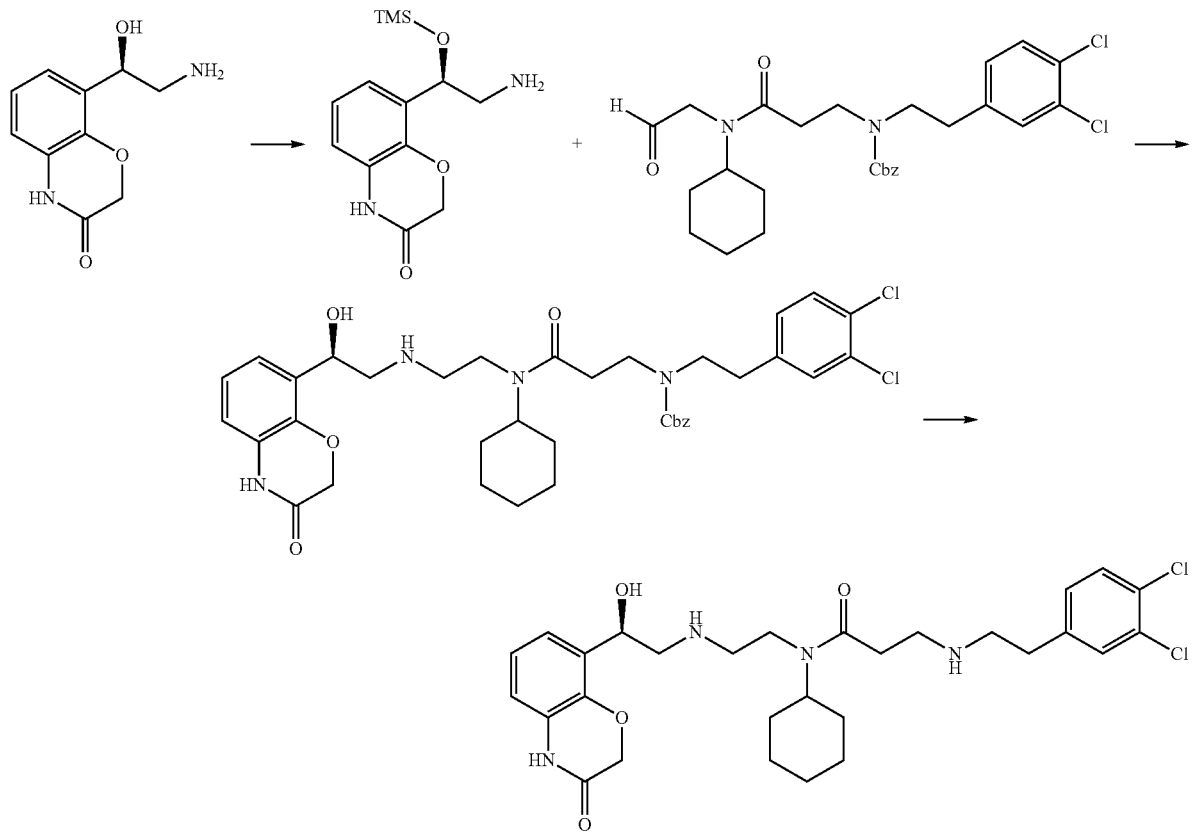

Scheme 4.

Step 1: (R)-8-(2-amino-1-(trimethylsilyloxy)ethyl)-2H-benzo[b][1,4]oxazin-3(4H)-one (R)-8-(2-amino-1-hydroxyethyl)-2H-benzo[b][1,4]oxazin-3(4H)-one was prepared via the same procedure as (S)-8-(2-amino-1-(trimethylsilyloxy)ethyl)-2H-benzo[b][1,4]oxazin-3(4H)-one, using instead (R)-8-(2-amino-1-hydroxyethyl)-2H-benzo[b][1,4]oxazin-3(4H)-one, MS (ESI) m/z 281 [M+H]$^+$.

Step 2: (R)-benzyl 3-(cyclohexyl(2-(2-hydroxy-2-(3-oxo-3,4-dihydro-2H-benzo[b][1,4]oxazin-8-yl)ethylamino)ethyl)amino)-3-oxopropyl(3,4-dichlorophenethyl)carbamate The title compound was prepared according to the procedure described for (S)-benzyl 3-(cyclohexyl(2-(2-hydroxy-2-(3-oxo-3,4-dihydro-2H-benzo[b][1,4]oxazin-8-yl)ethylamino)ethyl)amino)-3-oxopropyl(3,4-dichlorophenethyl)carbamate using instead (R)-8-(2-amino-1-(trimethylsilyloxy)ethyl)-2H-benzo[b][1,4]oxazin-3(4H)-one. $^1$H NMR (400 MHz, MeOD): δ 7.31-7.18 (m, 7H), 7.11-6.88 (m, 3H), 6.78-6.76 (m, 1H), 5.04-4.92 (m, 3H), 4.49 (d, J=7.2 Hz, 2H), 3.47-3.38 (m, 6H), 2.95-2.48 (m, 8H), 1.71-1.19 (m, 9H). MS (ES) m/z 713 [M+H]$^+$.

Step 3: (R)-N-cyclohexyl-3-(3,4-dichlorophenethylamino)-N-(2-(2-hydroxy-2-(3-oxo-3,4-dihydro-2H-benzo[b][1,4]oxazin-8-yl)ethylamino)ethyl)-propanamide The title compound was prepared according to the procedure described for (S)-N-cyclohexyl-3-(3,4-dichlorophenethylamino)-N-(2-(2-hydroxy-2-(3-oxo-3,4-dihydro-2H-benzo[b][1,4]oxazin-8-yl)ethylamino)ethyl)propanamide using instead (R)-benzyl 3-(cyclohexyl(2-(2-hydroxy-2-(3-oxo-3,4-dihydro-2H-benzo-[b][1,4]oxazin-8-yl)ethylamino)ethyl)amino)-3-oxopropyl(3,4-dichloro-phenethyl) carbamate. $^1$H NMR (400 MHz, MeOD): δ 7.34-7.31 (m, 2H), 7.09-7.06 (t, J=8.0 Hz, 2H), 6.88 (t, J=8.0 Hz, 1H), 6.75-6.72 (dd, J$_1$=8.0 Hz, J$_1$=1.2 Hz, 1H), 5.05-5.02 (dd, J$_1$=8.8 Hz, J$_1$=4.0 Hz, 1H), 4.54-4.44 (m, 2H), 3.56-3.50 (m, 1H), 3.31-3.20 (m, 2H), 2.82-2.66 (m, 11H), 2.55-2.51 (m, 2H), 1.80-1.10 (m, 11H). MS (ESI) m/z 579 [M+H]$^+$.

Example 2

N-cyclohexyl-3-(3,4-dichlorobenzyl)amino)-N-(2-((2-(5-hydroxy-3-oxo-3,4-dihydro-2H-benzo[b][1,4]oxazin-8-yl)ethyl)amino)-ethyl)propanamide The title compound was prepared according to the following procedure, as well as Schemes 5 and 6.

Scheme 5.
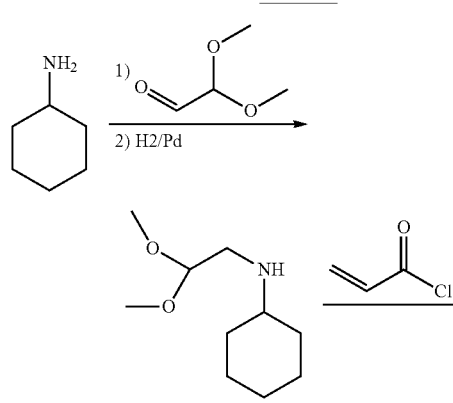
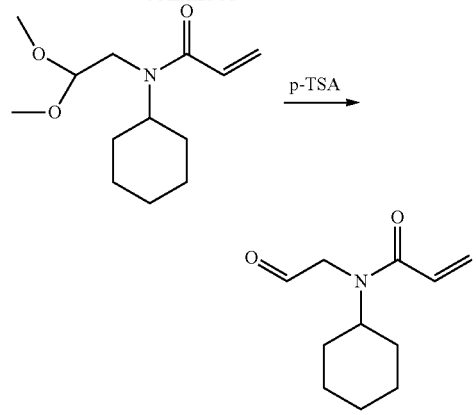
Scheme 6.
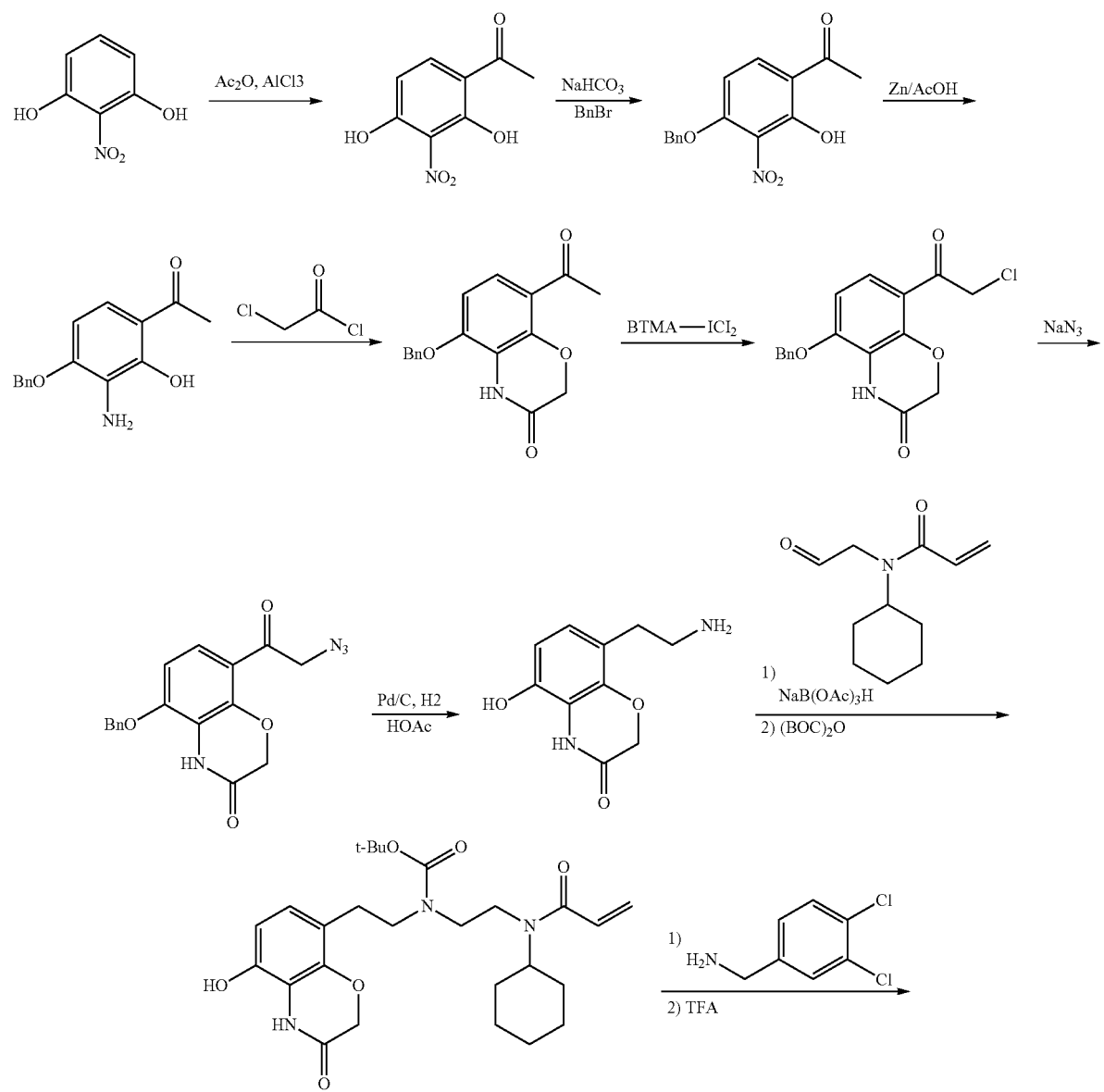

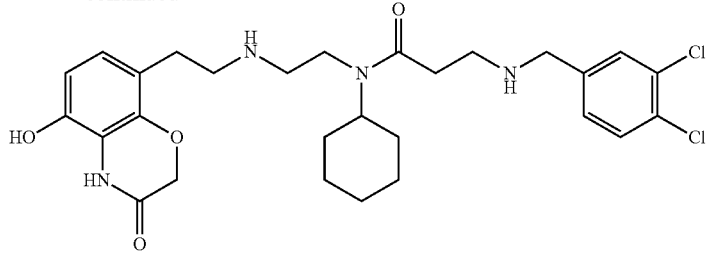

Step 1: N-(2,2-dimethoxyethyl)cyclohexanamine

A mixture of 2,2-dimethoxyacetaldehyde (3.00 g, 50.4 mmol) and cyclohexanamine (5.00 g, 50.4 mmol) in methanol (50 ml) was stirred at room temperature for 16 hours to give a yellow solution. Pd/C (0.537 g, 5.04 mmol) was added. The mixture was hydrogenated for 24 hours at 2 bar. The mixture was filtered, and the filtrate was concentrated under reduced pressure to afford the title compound (8.0 g, 42.7 mmol, 85% yield) as an oil, which was used further without purification.

Step 2: N-cyclohexyl-N-(2,2-dimethoxyethyl)acrylamide

To a mixture of N-(2,2-dimethoxyethyl)cyclohexanamine (6.5 g, 34.7 mmol) and methylamine (7.01 g, 69.4 mmol) in THF (50 mL) was added acryloyl chloride (3.30 g, 36.4 mmol). The mixture was stirred at room temperature for 16 hours to give a yellow solution. The mixture was diluted with 100 mL of ethyl acetate. The organic phase was washed with 100 mL of sat. NaHCO$_3$ was added and brine, dried over Na$_2$SO$_4$ and filtered. The filtrate was concentrated and the residue was purified by column chromatography on silica gel, eluting with pet. ether:EtOAc=1:1 to afford the title compound (3.15 g, 13.1 mmol, 38% yield) as an oil, MS (ESI+) 242 [M+H]$^+$.

Step 3: N-cyclohexyl-N-(2-oxoethyl)acrylamide

A mixture of N-cyclohexyl-N-(2,2-dimethoxyethyl)acrylamide (5.50 g, 22.8 mmol) and para-toluenesulfonic acid (3.92 g, 22.8 mmol) in dichloromethane (100 mL) was stirred at room temperature for 16 hours to give a yellow solution. The solution was diluted with additional dichloromethane, and washed with saturated aqueous sodium bicarbonate and brine. The organic layer was dried and concentrated to afford the crude product, which was purified via column chromatography on silica gel (pet. Ether:ethyl acteate=1:1) to afford the title compound (1.10 g, 5.64 mmol, 25% yield) as an oil. MS (ESI+) 196 [M+H]$^+$.

Step 4: 1-(2,4-dihydroxy-3-nitrophenyl)ethanone

To a vigorously stirred solution of aluminum chloride (46.3 g, 348 mmol) in nitrobenzene (325 mL) was added 2-nitrobenzene-1,3-diol (24.5 g, 158 mmol) portionwise over 15 minutes. This was followed by the addition of acetic anhydride (15.6 mL) over 15 min. The resultant mixture was then heated to 100° C. for 5 hours. The reaction was cooled to room temperature and carefully quenched with ice-cooled 2M hydrochloric acid (300 mL). The mixture was extracted with ether (2×500 mL) and the combined ether extracts were then washed with 2 M aqueous sodium hydroxide (2×400 mL). The combined aqueous layers were washed with ether and acidified to pH=1 with 2 M hydrochloric acid (700 mL). The resulting precipitate was filtered, washed with water, and dried under vacuum at 40° C. to afford the title compound (29.5 g, 150 mmol, 95% yield) as a brown solid. MS (ESI+) 198 [M+H]$^+$.

Step 5: 1-(4-(benzyloxy)-2-hydroxy-3-nitrophenyl)ethanone

To a solution of 1-(2,4-dihydroxy-3-nitrophenyl)ethanone (100 g, 508 mmol) in acetonitrile (700 mL) was added sodium bicarbonate (49.0 g, 583 mmol). The mixture was heated to 60° C. and benzyl bromide (75.6 mL) added. The mixture was then heated to reflux for 6.5 hours, and then cooled to 60° C. Water (450 mL) was then added, and the mixture was cooled to below 45° C. At this point, methyl tert-butyl ether (450 mL) added and the mixture was cooled to 20° C. and stirred for another 1.5 hours. The suspension was then filtered and washed with water (250 mL) then ethanol (250 mL) to yield the title compound. MS (ESI+) 288 [M+H]$^+$.

Step 6: 1-(3-amino-4-(benzyloxy)-2-hydroxyphenyl)ethanone

Zinc dust (5.50 g, 84.1 mmol) was added portion wise to a suspension of 1-(4-(benzyloxy)-2-hydroxy-3-nitrophenyl)ethanone (5.50 g, 19.2 mmol) in acetic acid (55 mL) over 15 minutes, while maintaining the internal temperature below 40° C. with an ice bath. The mixture was allowed to warm to room temperature and stirred for a further 2 hours. The mixture was filtered through Celite and washed with acetic acid. The filtrate was then poured onto ice/water (500 mL). The resulting precipitate was filtered off, washed with water, and dried under vacuum at 40° C. to afford the title compound (4.80 g, 18.7 mmol, 97% yield) as a light brown solid. MS (ESI+) 258 [M+H]$^+$.

Step 7: 8-acetyl-5-(benzyloxy)-2H-benzo[b][1,4]oxazin-3(4H)-one

2-Chloroacetyl chloride (1.77 mL) was added dropwise to a stirred mixture of 1-(3-amino-4-(benzyloxy)-2-hydroxyphenypethanone (5.20 g, 20.2 mmol) and sodium hydrogen carbonate (3.74 g, 44.5 mmol) in DMF (30 mL) and then stirred for a further two hours. Cesium carbonate (7.90 g, 24.2 mmol) was added and the mixture was heated at 100° C. for 20 hours. The mixture was cooled to room temperature, quenched with water (500 mL), extracted with ethyl acetate (2×200 mL), and the combined organic layers washed with water (3×300 mL) and brine. The organic layer was then dried over anhydrous sodium sulfate, filtered and evaporated in vacuo. The solid residue was treated with ether, filtered and the eluent dried to afford the title compound (5.70 g, 19.2 mmol, 95% yield) as a beige solid. MS (ESI+) 298 [M+H]+.

Step 8: 5-(benzyloxy)-8-(2-chloroacetyl)-2H-benzo [b][1,4]oxazin-3(4H)-one

Benzyltrimethylammonium dichloroiodate (14.2 g, 40.8 mmol) was added to a stirred solution of 8-acetyl-5-(benzyloxy)-2H-benzo[b][1,4]oxazin-3(4H)-one (5.50 g, 18.5 mmol) in a mixture of dichloromethane (100 mL), acetic acid (33 mL) and water (5.5 mL). The reaction mixture was stirred at 65° C. for 20 hours. The reaction was then cooled to room temperature, treated with aqueous sodium bisulphate (5.78 g, in 100 mL), and stirred for another 30 minutes. The mixture was diluted with ether (200 mL) and the resulting solid was filtered off, washed with water, then ether, and dried under vacuum at 40° C. to afford the title compound (5.60 g, 17.4 mmol, yield 94% yield) as a yellow solid. MS (ESI+) 332 [M+H]+.

Step 9: 8-(2-azidoacetyl)-5-(benzyloxy)-2H-benzo [b][1,4]oxazin-3(4H)-one

Sodium azide (1.18 g, 18.2 mmol) was added to a suspension of 5-(benzyloxy)-8-(2-chloroacetyl)-2H-benzo [b][1,4]oxazin-3(4H)-one (4.80 g, 14.5 mol) in DMF (50 mL) and the resulting mixture was stirred for 2 hours at room temperature. The mixture was poured onto ice water and the resulting solid was filtered off, washed with water and dried under vacuum at 40° C. to afford the title compound (4.60 g, 13.6 mmol, 94% yield) as an off-white solid. MS (ESI+) 339 [M+H]+.

Step 10: 8-(2-aminoethyl)-5-hydroxy-2H-benzo[b] [1,4]oxazin-3(4H)-one

A slurry of 10% palladium on carbon (1 gram) in acetic acid (20 mL) was added to a mixture of 8-(2-azidoacetyl)-5-(benzyloxy)-2H-benzo[b][1,4]oxazin-3(4H)-one (5.56 g, 16.4 mmol) in acetic acid (280 mL), followed by concentrated hydrochloric acid (14.3 mL). The mixture was stirred under a hydrogen atmosphere (5 bar) for 6 hours. Water (50 mL) was then added to dissolve any solid, followed by the addition of 10% palladium on carbon (1 g). The resultant mixture was stirred under a hydrogen atmosphere (5 bar) for another 20 hours. The mixture was filtered through celite and the filtrate concentrated in vacuo. The solid residue was treated with ether, collected by filtration, and dried to afford the title compound (2.20 g, 10.6 mmol, 65% yield) as a white solid. MS (ESI+) 209 [M+H]+.

Step 11: tert-butyl(2-(N-cyclohexylacrylamido) ethyl)(2-(5-hydroxy-3-oxo-3,4-dihydro-2H-benzo[b] [1,4]oxazin-8-yl)ethyl)carbamate In a in a mixture of NMP (20 mL), and water (2 mL) was dissolved 8-(2-aminoethyl)-5-hydroxy-2H-benzo[b][1,4]oxazin-3(4H)-one (2.10 g, 10.1 mmol) and N-cyclohexyl-N-(2-oxoethyl)acrylamide (2.00 g, 10.3 mmol). To this was added sodium bicarbonate (793 mg, 9.44 mmol) and the reaction was stirred for 15 minutes. Sodium triacetoxyborohydride (2.73 g, 12.9 mmol) was then added, and the resulting mixture was stirred for another 20 hours. The mixture was diluted with ethyl acetate (50 mL) and a solution of sodium bicarbonate (3.61 g) in water (50 mL) was added, followed by di-tert-butyl dicarbonate (2.25 g, 10.3 mmol). After stirring for 2 hours more, the mixture was diluted with ethyl acetate (100 mL) and washed with water and brine. The organic phase was dried over anhydrous sodium sulfate and evaporated in vacuo. The residue was purified by column chromatography on silica gel (eluting with pet. ether ethyl actate=2:1) to afford the title compound (870 mg, 1.78 mmol, 17% yield) as a white solid. MS (ESI+) 488 [M+H]+.

Step 12: N-cyclohexyl-3-((3,4-dichlorobenzyl) amino)-N-(2-((2-(5-hydroxy-3-oxo-3,4-dihydro-2H-benzo[b][1,4]oxazin-8-yl)ethyl)amino)ethyl)-propanamide tert-butyl(2-(N-cyclohexylacrylamido)ethyl)(2-(5-hydroxy-3-oxo-3,4-dihydro-2H-benzo[b][1,4]oxazin-8-yl) ethyl)carbamate (100 mg, 0.205 mmol) and (3,4-dichlorophenyl)methanamine (72 mg, 0.41 mmol) were dissolved in ethanol (1 mL) and heated at 50° C. for 20 hours. The solvent was evaporated in vacuo and the residue dissolved in dichloromethane (1 mL). Trifluoroacetic acid (1 mL, 13 mmol) was added and the mixture stirred for 2 hours, and then concentrated under reduced pressure. The residue was purified by prep-HPLC with (eluting with acetonitrile and 0.2% aqueous trifluoroacetic acid) to afford the title compound (125 mg, 0.155 mmol, 76% yield) as a white solid. $^1$H NMR (400 MHz, DMSO-$d_6$) δ 10.04-9.98 (m, 1H), 9.94-9.84 (m, 1H), 8.81 (s, 2H), 8.43 (s, 1H), 7.88-7.80 (m, 1H), 7.80-7.72 (m, 1H), 7.56-7.46 (m, 1H), 6.70-6.62 (m, 1H), 6.52-6.41 (m, 1H), 4.57-4.48 (m, 2H), 4.27-4.18 (m, 2H), 3.56-3.41 (m, 1H), 3.17-3.03 (m, 5H), 2.98 (d, J=12.0 Hz, 2H), 2.76 (dq, J=14.9, 6.9 Hz, 4H), 1.82-1.74 (m, 2H), 1.71-1.58 (m, 3H), 1.56-1.17 (m, 4H), 1.15-1.03 (m, 1H). MS (ESI+) 563.3 [M+H]+.

Example 3

N-cyclopentyl-N-(2-((2-(5-hydroxy-3-oxo-3,4-dihydro-2H-benzo[b][1,4]oxazin-8-yl)ethyl)amino) ethyl)-3-(phenethylamino)-propanamide The title compound was prepared by a procedure analogous to that reported for N-cyclohexyl-3-((3,4-dichlorobenzyl)amino)-N-(2-((2-(5-hydroxy-3-oxo-3,4-dihydro-2H-benzo[b][1,4]oxazin-8-yl)ethyl)amino)ethyl)propanamide, substituting cyclopentylamine for cyclohexylamine and 2-phenylethanamine for (3,4-dichlorophenyl)methanamine. $^1$H NMR (400 MHz, DMSO-$d_6$) δ 10.06-9.92 (m, 1H), 8.49-8.44 (m, 3H), 7.41-7.23 (m, 5H), 6.71-6.63 (m, 1H), 6.53-6.42 (m, 1H), 4.54 (s, 2H), 3.41 (dd, J=14.6, 5.2 Hz, 2H), 3.19 (s, 5H), 3.11-2.88 (m, 6H), 2.86-2.68 (m, 4H), 1.97-1.92 (m, 1H), 1.86-1.81 (m, 1H), 1.71-1.66 (m, 2H), 1.60-1.45 (m, 4H). MS (ES) 495.2 [M+H]+.

Example 4

N-cyclopentyl-3-((3,4-dichlorophenethyl)amino)-N-(2-((2-(5-hydroxy-3-oxo-3,4-dihydro-2H-benzo[b] [1,4]oxazin-8-yl)ethyl)amino)-ethyl)-propanamide The title compound was prepared by a procedure analogous to that reported for N-cyclohexyl-3-((3,4-dichlorobenzyl)amino)-N-(2-((2-(5-hydroxy-3-oxo-3,4-dihydro-2H-benzo[b][1,4]oxazin-8-yl)ethyl)amino)ethyl)propanamide, substituting cyclopentylamine for cyclonexylamine and 2-(3,4-dichloropheny)ethanamine for (3,4-dichlorophenyl) methanamine. $^1$H NMR (400 MHz, DMSO-$d_6$) δ 10.08-9.98

(m, 2H), 8.57-8.46 (m, 3H), 7.71-7.63 (m, 2H), 7.39-7.29 (m, 1H), 6.72 (dd, J=8.3, 4.1 Hz, 1H), 6.53 (dd, J=8.3, 4.1 Hz, 1H), 4.59 (d, J=1.8 Hz, 2H), 3.35-3.15 (m, 7H), 3.17-2.92 (m, 6H), 2.93-2.67 (m, 5H), 1.64-1.54 (m, 4H). MS (ESI$^+$) 563.3 [M+H]$^+$.

Example 5

N-cyclohexyl-3-((3,4-dichlorophenethyl)amino)-N-(2-((3-(piperidin-1-yl)propyl)amino)ethyl)propanamide The title compound was prepared by a procedure analogous to that reported for (S)-N-cyclohexyl-3-(3,4-dichlorophenethylamino)-N-(2-(2-hydroxy-2-(3-oxo-3,4-dihydro-2H-benzo[b][1,4]oxazin-8-yl)ethylamino)ethyl) propanamide, substituting 3-(piperidin-1-yl)propan-1-amine for (S)-8-(2-amino-1-hydroxyethyl)-2H-benzo[b][1,4]oxazin-3(4H)-one. $^1$H NMR (400 MHz, DMSO-d$_6$) δ 8.65-8.56 (m, 2H), 7.62-7.56 (m, 1H), 7.37 (d, J=2.3 Hz, 1H), 5.73 (s, 1H), 3.25-2.73 (m, 20H), 2.12-1.38 (m, 15H), 1.39-1.24 (m, 2H). MS (ESI+) 511.2 [M+H]$^+$.

Example 6

N-cyclohexyl-3-((3,4-dichlorophenethyl)amino)-N-(2-((2-(pyrrolidin-1-yl)ethyl)amino)ethyl)propanamide The title compound was prepared by a procedure analogous to that reported for (S)-N-cyclohexyl-3-(3,4-dichlorophenethylamino)-N-(2-(2-hydroxy-2-(3-oxo-3,4-dihydro-2H-benzo[b][1,4]oxazin-8-yl)ethylamino)ethyl) propanamide, substituting 2-(pyrrolidin-1-yl)ethanamine for (S)-8-(2-amino-1-hydroxyethyl)-2H-benzo[b][1,4]oxazin-3 (4H)-one. $^1$H NMR (400 MHz, DMSO-d$_6$) δ 9.13-8.50 (m, 3H), 7.60 (dd, J=6.4, 3.2 Hz, 1H), 7.39 (d, J=3.5 Hz, 1H), 3.83-3.47 (m, 2H), 3.26-2.71 (m, 13H), 2.38-1.18 (m, 13H), 1.16-1.01 (m, 1H). MS (ESI+) 483.2 [M+H]$^+$.

Example 7

N-(2-((4-cyanobenzyl)amino)ethyl)-N-cyclohexyl-((3,4-dichlorophenethyl)amino)propanamide The title compound was prepared by a procedure analogous to that reported for (S)-N-cyclohexyl-3-(3,4-dichlorophenethylamino)-N-(2-(2-hydroxy-2-(3-oxo-3,4-dihydro-2H-benzo[b][1,4]oxazin-8-yl)ethylamino)ethyl) propanamide, substituting 4-(aminomethyl)benzonitrile for (S)-8-(2-amino-1-hydroxyethyl)-2H-benzo[b][1,4]oxazin-3 (4H)-one. $^1$H NMR (400 MHz, DMSO-d$_6$) δ 9.10-8.80 (m, 1H), 8.53-8.26 (m, 2H), 7.97 (d, J=8.0 Hz, 1H), 7.95-7.80 (m, 1H), 7.68 (d, J=8.0 Hz, 1H), 7.66-7.52 (m, 2H), 7.46 (d, J=7.7 Hz, 1H), 7.33-7.20 (m, 1H), 4.35-4.21 (m, 1H), 3.30-2.66 (m, 11H), 2.13-1.88 (m, 1H), 1.89-1.18 (m, 10H), 1.19-1.00 (m, 1H). MS (ESI+) 501.1 [M+H]$^+$.

Example 8

N-cyclohexyl-3-((3,4-dichlorophenethyl)amino)-N-(2-((6-methyl-3-neopentyl-4,5,6,7-tetrahydropyrazolo[1,5-a]pyrimidin-2-yl)-amino)ethyl)-propanamide The title compound was prepared by a procedure analogous to that reported for (S)-N-cyclohexyl-3-(3,4-dichlorophenethylamino)-N-(2-(2-hydroxy-2-(3-oxo-3,4-dihydro-2H-benzo[b][1,4]oxazin-8-yl)ethylamino)ethyl) propanamide, substituting 6-methyl-3-neopentyl-4,5,6,7-tetrahydropyrazolo[1,5-a]pyrimidin-2-amine for (S)-8-(2-amino-1-hydroxyethyl)-2H-benzo[b][1,4]oxazin-3(4H)-one. NMR (501 MHz, DMSO-d$_6$) δ 8.72 (bs, 1H), 7.59 (dd, J=7.3, 2.2 Hz, 1H), 7.43-7.28 (m, 2H), 7.27-7.03 (m, 1H), 4.19-3.49 (m, 3H), 3.32-2.97 (m, 10H), 2.99-2.76 (m, 2H), 2.25-2.16 (m, 1H), 2.12-2.07 (m, 2H), 1.83-1.40 (m, 8H), 1.42-1.19 (m, 2H), 1.17-0.90 (m, 3H), 0.89-0.82 (m, 9H). MS (ESI+) 591.2 [M+H]$^+$.

Example 9

(S)-N-cyclohexyl-3-(phenethylamino)-N-(2-(2-((pyridin-3-yloxy)methyl)azetidin-1-yl)ethyl)propanamide The title compound was prepared by a procedure analogous to that reported for (S)-N-cyclohexyl-3-(3,4-dichlorophenethylamino)-N-(2-(2-hydroxy-2-(3-oxo-3,4-dihydro-2H-benzo[b][1,4]oxazin-8-yl)ethylamino)ethyl) propanamide, substituting (S)-3-(azetidin-2-ylmethoxy) pyridine for 8(S)-8-(2-amino-1-hydroxyethyl)-2H-benzo[b][1,4]oxazin-3(4H)-one and 2-phenylethanamine for 2-(3,4-dichlorophenyl)ethanamine. $^1$H NMR (400 MHz, DMSO-d$_6$) δ 8.44-8.34 (m, 3H), 8.26 (d, J=3.5 Hz, 1H), 7.49-7.31 (m, 5H), 7.31-7.25 (m, 4H), 4.47-4.40 (m, 2H), 3.25-3.13 (m, 7H), 2.96-2.88 (m, 4H), 2.85-2.75 (m, 3H), 1.83-1.74 (m, 3H), 1.71-1.58 (m, 4H). MS (ESI+) 465.2 [M+H]$^+$.

Example 10

N-cyclohexyl-N-(2-((2-(5-hydroxy-3-oxo-3,4-dihydro-2H-benzo[b][1,4]oxazin-8-yl)ethyl)amino) ethyl)-3-methoxypropanamide The title compound was prepared by a procedure analogous to that reported for tert-butyl(2-(N-cyclohexylacrylamido)ethyl)(2-(5-hydroxy-3-oxo-3,4-dihydro-2H-benzo[b][1,4]oxazin-8-yl)ethyl)carbamate, and by stirring the compound in methanol/dichloromethane followed by Cbz deprotection to furnish the title compound. $^1$H NMR (500 MHz, DMSO-d$_6$) δ 9.48 (bs, 1H), 8.69-8.31 (m, 2H), 6.67 (d, J=8.3 Hz, 1H), 6.49 (d, J=8.3 Hz, 1H), 4.54 (s, 2H), 4.09-3.50 (m, 3H), 3.50-3.43 (m, 2H), 3.15-2.96 (m, 4H), 2.91-2.78 (m, 2H), 2.64-2.57 (m, 1H), 1.82-1.18 (m, 9H), 1.14-0.98 (m, 1H). MS (ESI+) 420.1 [m+H]$^+$.

Example 11

N-cyclohexyl-N-(2-((2-(5-hydroxy-3-oxo-3,4-dihydro-2H-benzo[b][1,4]oxazin-8-yl)ethyl)amino) ethyl)-3-(phenethylamino)-propanamide The title compound was prepared by a procedure analogous to that reported for N-cyclohexyl-3-((3,4-dichlorobenzyl)amino)-N-(2-((2-(5-hydroxy-3-oxo-3,4-dihydro-2H-benzo[b][1,4]oxazin-8-yl)ethyl)amino)ethyl)propanamide, substituting 2-phenylethanamine for (3,4-dichlorophenyl) methanamine. $^1$H NMR (400 MHz, DMSO-d$_6$) δ 10.02-9.96 (m, 2H), 8.49 (bs, 3H), 7.37-7.30 (m, 2H), 7.29-7.21 (m, 3H), 6.64 (d, J=8.2 Hz, 1H), 6.46 (d, J=8.3 Hz, 1H), 4.52 (s, 2H), 3.28-2.84 (m, 10H), 2.86-2.68 (m, 4H), 1.83-1.16 (m, 9H), 1.12-1.00 (m, 1H). MS (ESI+) 509.2 [M+H]$^+$.

Example 12

N-cyclohexyl-3-((3,4-dichlorophenethyl)amino)-N-(2-(4-(indolin-4-yl)piperazin-1-yl)ethyl)propanamide The title compound was prepared by a procedure analogous to that reported for (S)-N-cyclohexyl-3-(3,4-dichlorophenethylamino)-N-(2-(2-hydroxy-2-(3-oxo-3,4-dihydro-2H-benzo[b][1,4]oxazin-8-yl)ethylamino)ethyl) propanamide, substituting 4-(piperazin-1-yl)indoline dihydrochloride for (S)-8-(2-amino-1-hydroxyethyl)-2H-benzo[b][1,4]oxazin-3(4H)-one. $^1$H NMR (400 MHz, DMSO-$d_6$) δ 8.74-8.49 (m, 3H), 7.63-7.57 (m, 1H), 7.44-7.34 (m, 2H), 7.03-6.94 (m, 1H), 6.40-6.24 (m, 2H), 3.26-2.97 (m, 16H), 2.89-2.79 (m, 4H), 1.85-1.24 (m, 9H), 1.21-1.06 (m, 1H). MS (ESI+) 572.22 [M+H]$^+$.

Example 13

N-cyclohexyl-3-((3,4-dichlorophenethyl)amino)-N-(2-((3-(pyrrolidin-1-yl)propyl)amino)ethyl)propanamide The title compound was prepared by a procedure analogous to that reported for (S)-N-cyclohexyl-3-(3,4-dichlorophenethylamino)-N-(2-(2-hydroxy-2-(3-oxo-3,4-dihydro-2H-benzo[b][1,4]oxazin-8-yl)ethylamino)ethyl) propanamide, substituting 3-(pyrrolidin-1-yl)propan-1-amine for (S)-8-(2-amino-1-hydroxyethyl)-2H-benzo[b][1,4]oxazin-3(4H)-one. $^1$H NMR (400 MHz, DMSO-$d_6$) δ 8.79-8.64 (m, 3H), 7.65-7.55 (m, 1H), 7.43-7.33 (m, 2H), 3.28-2.90 (m, 15H), 2.92-2.72 (m, 2H), 2.09-1.22 (m, 14H). MS (ESI+) 497.1 [M+H]$^+$.

Example 14

N-cyclobutyl-N-(2-((2-(5-hydroxy-3-oxo-3,4-dihydro-2H-benzo[b][1,4]oxazin-8-yl)ethyl)amino)ethyl)-3-(phenethylamino)-propanamide The title compound was prepared by a procedure analogous to that reported for N-cyclohexyl-3-((3,4-dichlorobenzyl)amino)-N-(2-((2-(5-hydroxy-3-oxo-3,4-dihydro-2H-benzo[b][1,4]oxazin-8-yl)ethyl)amino)ethyl)propanamide, substituting cyclobutylamine for cyclohexylamine and 2-phenylethanamine for (3,4-dichlorophenyl)methanamine. $^1$H NMR (400 MHz, DMSO-$d_5$) δ 10.03-9.86 (m, 2H), 8.66-8.51 (m, 4H), 7.40-7.32 (m, 2H), 7.31-7.25 (m, 3H), 6.67 (d, J=8.2 Hz, 1H), 6.47 (d, J=8.0 Hz, 1H), 4.56-4.49 (m, 2H), 3.27-3.03 (m, 5H), 2.97-2.87 (m, 4H), 2.78-2.69 (m, 3H), 2.42-1.86 (m, 5H), 1.86-1.53 (m, 2H). MS (ESI+) 481.1 [M+H]$^+$.

Example 15

N-cyclobutyl-3-((3,4-dichlorophenethyl)amino)-N-(2-((2-(5-hydroxy-3-oxo-3,4-dihydro-2H-benzo[b][1,4]oxazin-8-yl)ethyl)amino)-ethyl)-propanamide The title compound was prepared by a procedure analogous to that reported for N-cyclohexyl-3-((3,4-dichlorobenzyl)amino)-N-(2-((2-(5-hydroxy-3-oxo-3,4-dihydro-2H-benzo[b][1,4]oxazin-8-yl)ethyl)amino)ethyl)propanamide, substituting cyclobutylamine for cyclohexylamine and 2-(3,4-dichlorophenyl)ethanamine for (3,4-dichlorophenyl)methanamine. $^1$H NMR (400 MHz, DMSO-$d_6$) δ 10.02-9.80 (m, 2H), 8.64 (bs, 1H), 8.52 (bs, 2H), 7.63 (d, J=8.6 Hz, 1H), 7.63-7.59 (m, 1H), 7.33-7.27 (m, 1H), 6.67 (d, J=8.3 Hz, 1H), 6.47 (d, J=8.0 Hz, 1H), 4.56-4.49 (m, 2H), 3.17 (s, 7H), 3.12-2.81 (m, 4H), 2.83-2.63 (m, 4H), 2.34-1.99 (m, 4H), 2.01-1.54 (m, 2H). MS (ESI+) 549.2 [M+H]$^+$.

Example 16

N-cyclohexyl-3-((2,3-dichlorophenethyl)amino)-N-(2-((2-(2-methylindolizin-1-yl)ethyl)amino)ethyl)propanamide The title compound was prepared according to the following Scheme 7.

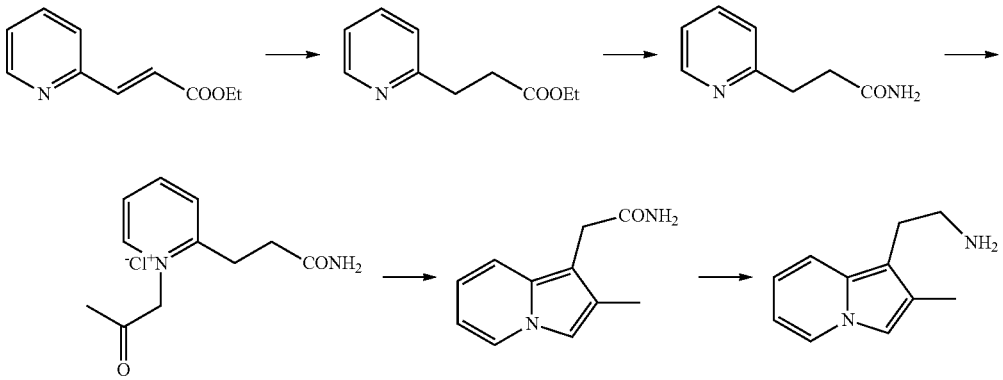

Scheme 7.

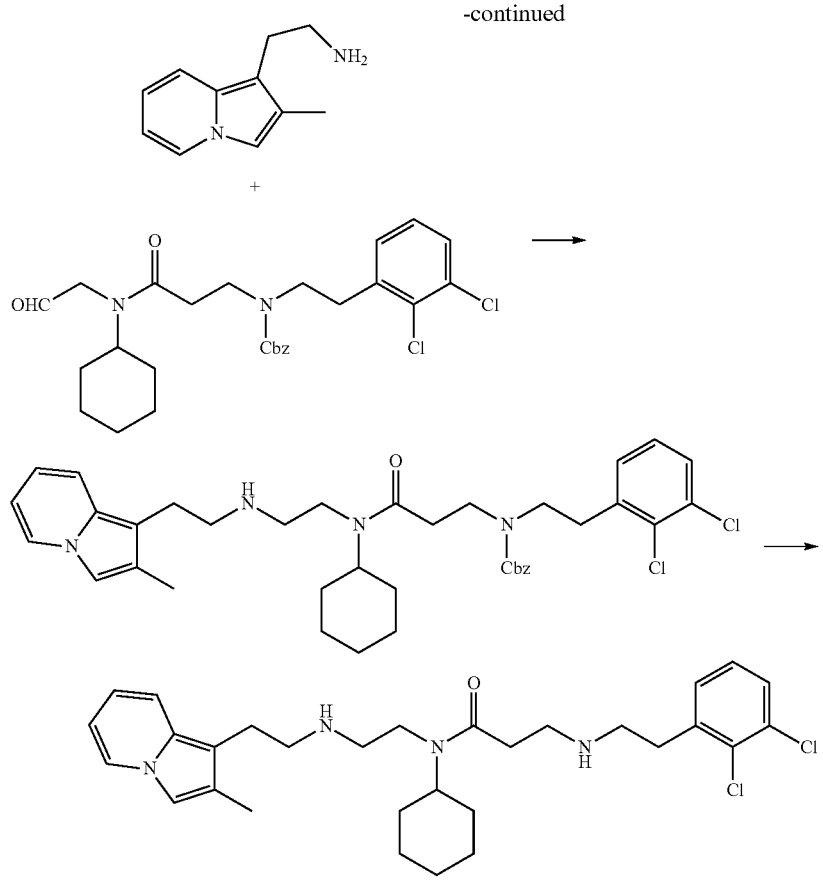

Step 1: Ethyl 3-(pyridin-2-yl)propanoate

To a solution of (E)-ethyl 3-(pyridin-2-yl)acrylate (150 g, 0.847 mol) in ethanol (1 L) was added Pd/C (90 g, 0.847 mol) under $N_2$, The resulting mixture was stirred under $H_2$ (50 psi) at 50° C. for 2 hours. TLC (petroleum ether:ethyl acetate=5:1) indicated that the reaction was completed. After filtration, the filtrate was concentrated to furnish the title compound (65 g, yield: 42.8%), which was used without further purification. MS (ESI+) 180 [M+H]+.

Step 2: 3-(pyridin-2-yl)propanamide

Ammonia (170 g, 10 mol) in methanol (1 L) was added to a stirred solution of ethyl 3-(pyridin-2-yl)propanoate (64.5 g, 0.36 mol) in methanol (1.5 L) in 100° C. over a period of 5 min. The mixture was allowed to warm to ambient temperature and stirred for 48 hrs. After cooling to room temperature, the mixture was concentrated in vacuum. The residue was purified by flash chromatography on silica gel (petroleum ether: EtOAc=5:1) to give the title compound (54 g, 0.360 mol, 100% yield) as a yellow solid, which was used without further purification. MS (ESI+) 151 [M+H]+.

Step 3: 2-(3-amino-3-oxopropyl)-1-(2-oxopropyl) pyridin-1-ium chloride

A solution of 3-(pyridin-2-yl)propanamide (20 g, 1.33 mmol) and 1-chloropropan-2-one (10 g, 108 mmol) in acetone (1000 mL) was refluxed for 24 hrs. TLC (ethyl acetate:methanol=6:1) showed the reaction was mostly complete. The solvent was removed by evaporation under reduced pressure to give the crude product (14 g, yield: 67.0%, 60% TLC purity) as a yellow solid, which was used without further purification. MS (ESI+) 208 [M+H]+.

Step 4: 2-(2-methylindolizin-1-yl)acetamide

A solution of 2-(3-amino-3-oxopropyl)-1-(2-oxopropyl) pyridin-1-ium chloride (14 g, 67.6 mmol) and $NaHCO_3$ (56 g, 0.67 mol) in ethanol (100 mL) was refluxed for 5 hours. TLC (ethyl acetate:methanol=6:1) showed the reaction was complete. The solvent was removed by evaporation under reduced pressure. The residue was purified by flash chromatography on silica gel (petroleum ether: EtOAc=5:1) to give the title compound (1.5 g, yield: 14%) as a yellow solid. $^1$H NMR (400 MHz, MeOD) δ 8.10-8.04 (m, 1H), 7.37 (d, J=9.3 Hz, 1H), 7.28 (s, 1H), 7.17 (br. s., 1H), 6.79 (br. s., 1H), 6.56 (ddd, J=0.9, 6.4, 9.0 Hz, 1H), 6.43-6.35 (m, 1H), 3.42 (s, 1H), 2.18 (s, 1H). MS (ESI+) 189 [M+H]+.

Step 5: 2-(2-methylindolizin-1-yl)ethanamine

To a solution of 2-(2-methylindolizin-1-yl)acetamide (4 g, 21.25 mmol) in THF (100 mL) was added $BH_3$.DMS (0.454 mL, 4.78 mmol). The mixture was stirred for overnight at 80° C. TLC (petroleum ether: ethyl acetate=1:1) showed the starting material was completely consumed. The mixture was quenched by the addition of water (20 mL) and a 15% sodium hydroxide solution (0.19 mL). The resulting mixture was filtered through celite and the filtrate was diluted with ethyl acetate (200 mL) and water (50 mL). The organic layer was washed with brine, dried over $Na_2SO_4$, concentrated and purified by column chromatography on silica gel (ethyl acetate:methanol=100:1) to give the title compound (0.9 g, yield: 24.31%) as yellow solid. $^1$H NMR (400 MHz, MeOD) δ 7.91 (d, J=7.1 Hz, 1H), 7.27 (d. J=9.3 Hz, 1H), 7.18 (s, 1H), 6.59-6.53 (m, 1H), 6.38-6.32 (m, 1H), 2.93-2.82 (m, 1H), 2.26-2.23 (m, 1H). MS (ESI+) 175 [M+H]$^+$.

Step 6: benzyl(3-(cyclohexyl(2-((2-(2-methylindolizin-1-yl)ethyl)-amino)ethyl)amino)-3-oxopropyl)(2,3-dichlorophenethyl)carbamate To a solution of benzyl(3-(cyclohexyl(2-oxoethyl)amino)-3-oxopropyl)(2,3-dichlorophenethyl)carbamate (1.8 g, 3.5 mmol) in methanol (20 mL) was added dropwise a solution of 2-(2-methylindolizin-1-yl)ethanamine (0.4 g, 2.3 mmol) in methanol (10 mL). The resulting suspension was stirred at ambient temperature for 2 hours. Then, sodium cyanoborohydride (218 mg, 3.5 mmol) was added, and the reaction mixture was stirred overnight. TLC (petroleum ether: ethyl acetate=5:1) showed the reaction was complete. The mixture was diluted with dichloromethane (100 mL) and washed with saturated sodium hydrogen carbonate, water and brine. The organic phase was dried over anhydrous sodium sulfate, filtered and concentrated in vacuum to afford the crude product (0.65 g, yield: 41.8%) as a yellow gum, which was used without further purification. $^1$H NMR (400 MHz, MeOD) δ7.77 (d, J=7.1 Hz, 1H), 7.42-7.28 (m, 6H), 7.16-6.99 (m, 3H), 6.58-6.52 (m, 1H), 6.38-6.32 (m, 1H), 5.19-5.01 (m, 2H), 3.61-3.47 (m, 5H), 3.35-3.23 (m, 2H), 3.15-2.46 (m, 11H), 2.30-2.24 (m, 2H), 1.86-1.54 (m, 7H), 1.49-1.24 (m, 5H), 1.19-0.96 (m, 1H). MS (ESI+) 678 [M+H]$^+$.

Step 7: N-cyclohexyl-3-((2,3-dichlorophenyl)amino)-N-(2-((2-(2-methylindolizin-1-yl)ethyl)amino)ethyl)propanamide To a solution of benzyl(3-(cyclohexyl(2-((2-(2-methylindolizin-1-yl)ethyl)amino)ethyl)amino)-3-oxopropyl)(2,3-dichlorophenethyl)carbamate (600 mg, 0.88 mmol) in acetic acid (3 mL) was added dropwise HBr/AcOH (3 mL, 13 mmol, content: 35%). The resulting suspension was stirred at ambient temperature for 2 hours, TLC (petroleum ether: EtOAc=1:1) showed the reaction was complete. The solvent was removed by evaporation under reduced pressure. The residue was then diluted with dichloromethane (100 mL) and washed sequentially with saturated sodium bicarbonate, water, and brine. The organic phase was dried over anhydrous sodium sulfate, filtered and concentrated in vacuum. The residue was purified by prep-HPLC to afford the title compound (34 mg, 0.706% yield) as a green gum. $^1$H NMR (400 MHz, MeOD) δ 11.88 (br. s., 2H), 9.40-8.88 (m, 6H), 7.38-6.99 (m, 6H), 3.59 (br. s., 3H), 3.45-3.18 (m, 9H), 3.09 (br. s., 6H), 2.88-2.73 (m, 3H), 2.18 (s, 3H), 1.82-1.51 (m, 7H), 1.37-0.93 (m, 8H). MS (ESI+) 543 [M+H]$^+$.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above products and methods without departing from the scope of the invention, it is intended that all matter contained in the above description and shown in the accompanying drawings shall be interpreted as illustrative and not in a limiting sense.

What is claimed is:
1. A compound having a structure of Formula (I):

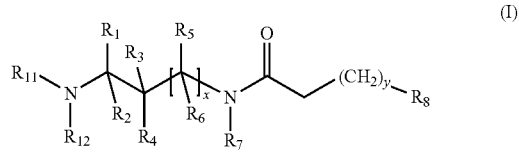

or a pharmaceutically acceptable salt thereof, wherein:
each of $R_1$, $R_2$, $R_3$, $R_4$, $R_5$, and $R_6$ are independently hydrogen or $C_{1-6}$ alkyl;
x has a value from 0 to 1;
y has a value from 0 to 3;
$R_7$ is a $C_4$-$C_6$ cycloalkyl;
$R_8$ is —$OR_9$ or —$NHR_{10}$;
$R_9$ is a $C_{1-10}$ alkyl;
$R_{10}$ is a $C_{1-2}$ alkyl substituted with a phenyl, wherein the phenyl is optionally further substituted with halogen; and,
(i) $R_{11}$ and $R_{12}$ are taken together with the nitrogen atom to which they are bound to form an optionally substituted heterocyclic ring having a structure:

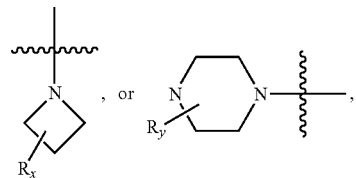

wherein $R_x$ is selected from hydrogen and methoxypyridinyl, and $R_y$ is selected from hydrogen and indolinyl; or alternatively,
(ii) one of $R_{11}$ and $R_{12}$ is hydrogen, and the other is selected from:
(a) a pyrazolopyrimidinyl ring having a structure:

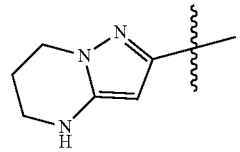 [SMILES: *c1cc2n(n1)CCCN2]

and being optionally substituted with one or more $C_{1-5}$ alkyl substituents; and,
(b) a $C_{1-3}$ substituted alkyl or a $C_{1-3}$ substituted hydoxyalkyl, wherein said substituent is selected from the group consisting of piperidinyl, pyrrolidinyl, cyanophenyl, methylindolizinyl, and a moiety having a structure:

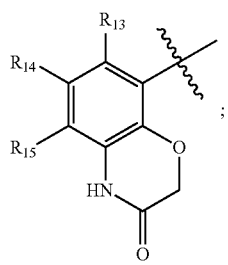

wherein $R_{13}$, $R_{14}$, and $R_{15}$ are each independently selected from hydrogen, halogen, hydroxyl, trifluoromethyl, cyano, carboxyl, $C_{1-6}$ alkyl, $C_{1-6}$ alkoxy, and $C_{1-6}$ alkylcarbonyl; provided that if one of $R_{11}$ and $R_{12}$ is $C_{1-3}$ substituted alkyl and $R_{15}$ is hydroxyl, then $R_7$ comprises a $C_4$ or $C_5$ unsubstituted cycloalkyl, or $R_8$ is —$OR_9$, or $R_8$ is —$NHR_{10}$, wherein $R_{10}$ is methyl substituted with a phenyl, optionally further substituted with a halogen.

2. The compound of claim 1, wherein $R_{11}$ and $R_{12}$ are taken together with the nitrogen atom to which they are bound to form a heterocyclic ring having the structure:

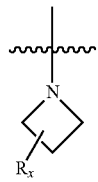

wherein $R_x$ comprises the following structure:

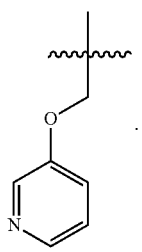

3. The compound of claim 1, wherein $R_{11}$ and $R_{12}$ are taken together with the nitrogen atom to which they are bound to form a heterocyclic ring having a structure:

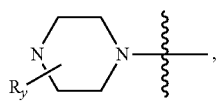

wherein $R_y$ comprises the following structure:

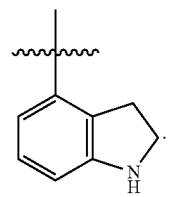 [SMILES: *c1cccc2c1CCN2]

4. The compound of claim 1, wherein one of $R_{11}$ and $R_{12}$ is hydrogen and the other comprises a pyrazolopyrimidinyl ring having a structure:

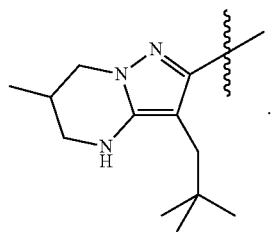 [SMILES: *c1nn2c(c1CC(C)(C)C)NCC(C)C2]

5. The compound of claim 1, wherein one of $R_{11}$ and $R_{12}$ is hydrogen and the other comprises a $C_{1-3}$ piperidinyl-substituted alkyl.

6. The compound of claim 1, wherein one of $R_{11}$ and $R_{12}$ is hydrogen and the other comprises a $C_{1-3}$ pyrrolidinyl-substituted alkyl.

7. The compound of claim 1, wherein one of $R_{11}$ and $R_{12}$ is hydrogen and the other comprises a $C_{1-3}$ cyanophenyl-substituted alkyl.

8. The compound of claim 1, wherein one of $R_{11}$ and $R_{12}$ is hydrogen and the other comprises a $C_{1-3}$ methylindolizinyl-substituted alkyl.

9. The compound of claim 1, wherein one of $R_{11}$ and $R_{12}$ is hydrogen and the other comprises a $C_{1-3}$ substituted alkyl comprising a substituent having the structure:

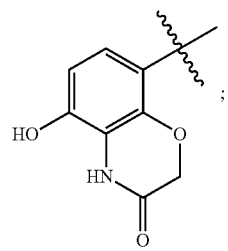

and $R_7$ comprises a $C_4$ or $C_5$ unsubstituted cycloalkyl.

10. The compound of claim 1, wherein one of $R_{11}$ and $R_{12}$ is hydrogen and the other comprises a $C_{1-3}$ substituted alkyl comprising a substituent having the structure:

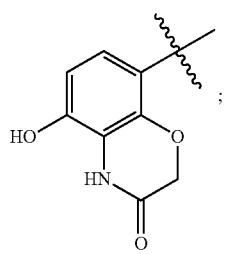 [SMILES: *c1ccc(O)c2c1OCC(=O)N2]

and R$_8$ is —OR$_9$.

11. The compound of claim 1, wherein one of R$_{11}$ and R$_{12}$ is hydrogen and the other comprises a C$_{1-3}$ substituted alkyl comprising a substituent having the structure:

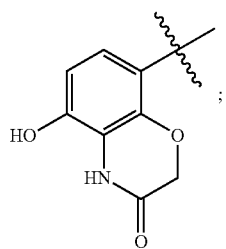 [SMILES: *c1ccc(O)c2c1OCC(=O)N2]

and R$_{10}$ is methyl substituted with an optionally substituted phenyl.

12. The compound of claim 1, wherein one of R$_{11}$ and R$_{12}$ is hydrogen and the other comprises a C$_{1-3}$ substituted hydroxyalkyl comprising a substituent having the structure:

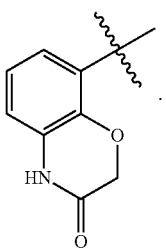 [SMILES: *c1cccc2c1OCC(=O)N2]

13. The compound selected from the group consisting of:
N-cyclohexyl-3-((3,4-dichlorophenethyl)amino)-N-(2-((2-hydroxy-2-(3-oxo-3,4-dihydro-2H-benzo[b][1,4]oxazin-8-yl)ethyl)amino)ethyl)propanamide;
N-cyclohexyl-3-((3,4-dichlorobenzyl)amino)-N-(2-((2-(5-hydroxy-3-oxo-3,4-dihydro-2H-benzo[b][1,4]oxazin-8-yl)ethyl)amino)ethyl)propanamide;
N-cyclopentyl-N-(2-((2-(5-hydroxy-3-oxo-3,4-dihydro-2H-benzo[b][1,4]oxazin-8-yl)ethyl)amino)ethyl)-3-(phenethylamino)propanamide;
N-cyclopentyl-3-((3,4-dichlorophenethyl)amino)-N-(2-((2-(5-hydroxy-3-oxo-3,4-dihydro-2H-benzo[b][1,4]oxazin-8-yl)ethyl)amino)ethyl)propanamide;
N-cyclohexyl-3-((3,4-dichlorophenethyl)amino)-N-(2-((3-(piperidin-1-yl)propyl)-amino)ethyl)propanamide;
N-cyclohexyl-3-((3,4-dichlorophenethyl)amino)-N-(2-((2-(pyrrolidin-1-yl)ethyl)-amino)ethyl)propanamide;
N-(2-((4-cyanobenzyl)amino)ethyl)-N-cyclohexyl-3-((3,4-dichlorophenethyl)-amino)propanamide;
N-cyclohexyl-3-((3,4-dichlorophenethyl)amino)-N-(2-((6-methyl-3-neopentyl-4,5,6,7-tetrahydropyrazolo[1,5-a]pyrimidin-2-yl)amino)ethyl)propanamide;
(S)-N-cyclohexyl-3-(phenethylamino)-N-(2-(2-((pyridin-3-yloxy)methyl)azetidin-1-yl)ethyl)propanamide;
(R)-N-cyclohexyl-3-(phenethylamino)-N-(2-(2-((pyridin-3-yloxy)methyl)-azetidin-1-yl)ethyl)propanamide;
N-cyclohexyl-N-(2-((2-(5-hydroxy-3-oxo-3,4-dihydro-2H-benzo[b][1,4]oxazin-8-yl)ethyl)amino)ethyl)-3-methoxypropanamide;
N-cyclohexyl-3-((3,4-dichlorophenethyl)amino)-N-(2-(4-(indolin-4-yl)piperazin-1-yl)ethyl)propanamide;
N-cyclohexyl-3-((3,4-dichlorophenethyl)amino)-N-(2-((3-(pyrrolidin-1-yl)-propyl)amino)ethyl)propanamide;
N-cyclobutyl-N-(2-((2-(5-hydroxy-3-oxo-3,4-dihydro-2H-benzo[b][1,4]oxazin-8-yl)ethyl)amino)ethyl)-3-(phenethylamino)propanamide;
N-cyclobutyl-3-((3,4-dichlorophenethyl)amino)-N-(2-((2-(5-hydroxy-3-oxo-3,4-dihydro-2H-benzo[b][1,4]oxazin-8-yl)ethyl)amino)ethyl)propanamide;
N-cyclohexyl-3-((2,3-dichlorophenethyl)amino)-N-(2-((2-(2-methylindolizin-1-yl)ethyl)amino)ethyl)propanamide;
and pharmaceutically acceptable salts thereof.

14. The compound (R)-N-cyclohexyl-3-((3,4-dichlorophenethyl)amino)-N-(2-((2-hydroxy-2-(3-oxo-3,4-dihydro-2H-benzo[b][1,4]oxazin-8-yl)ethyl)amino)ethyl)-propanamide, or a pharmaceutically acceptable salt thereof.

15. The compound (S)-N-cyclohexyl-3-((3,4-dichlorophenethyl)amino)-N-(2-((2-hydroxy-2-(3-oxo-3,4-dihydro-2H-benzo[b][1,4]oxazin-8-yl)ethyl)amino)ethyl)-propanamide, or a pharmaceutically acceptable salt thereof.

16. A pharmaceutical composition comprising a therapeutically effective dosage of the compound of claim 1, or a pharmaceutically effective salt thereof, and a pharmaceutically acceptable excipient.

17. A pharmaceutical composition comprising a compound of Formula (I):

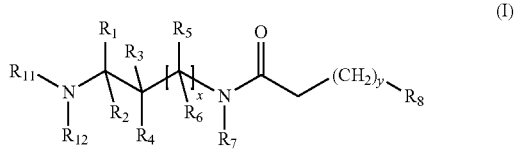

or a pharmaceutically acceptable salt thereof, and one or more pharmaceutically acceptable excipients, wherein:
each of R$_1$, R$_2$, R$_3$, R$_4$, R$_5$, and R$_6$ are independently hydrogen or C$_{1-6}$ alkyl;
x has a value from 0 to 1;
y has a value from 0 to 3;
R$_7$ is a C$_4$-C$_6$ cycloalkyl;
R$_8$ is —OR$_9$ or —NHR$_{10}$;
R$_9$ is a C$_{1-10}$ alkyl;
R$_{10}$ is a C$_{1-2}$ alkyl substituted with a phenyl, wherein the phenyl is optionally further substituted with halogen; and,
(i) R$_{11}$ and R$_{12}$ are taken together with the nitrogen atom to which they are bound to form an optionally substituted heterocyclic ring having a structure:

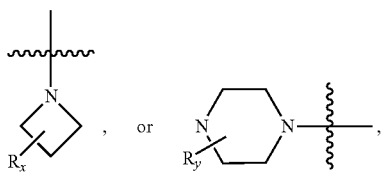

, or wherein $R_x$ is selected from hydrogen and methoxypyridinyl, and $R_y$ is selected from hydrogen and indolinyl; or alternatively, (ii) one of $R_{11}$ and $R_{12}$ is hydrogen, and the other is selected from:

(a) a pyrazolopyrimidinyl ring having a structure:

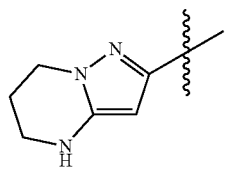 [SMILES: *c1cc2n(n1)CCCN2]

and being optionally substituted with one or more $C_{1-5}$ alkyl substituents; and, (b) a $C_{1-3}$ substituted alkyl or a $C_{1-3}$ substituted hydoxyalkyl, wherein said substituent is selected from the group consisting of piperidinyl, pyrrolidinyl, cyanophenyl, methylindolizinyl, and a moiety having a structure:

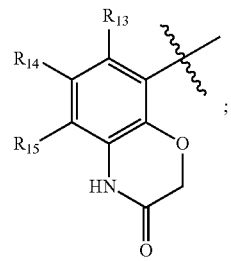

wherein $R_{13}$, $R_{14}$, and $R_{15}$ are each independently selected from hydrogen, halogen, hydroxyl, trifluoromethyl, cyano, carboxyl, $C_{1-6}$ alkyl, $C_{1-6}$ alkoxy, and $C_{1-6}$ alkylcarbonyl; provided that if one of $R_{11}$ and $R_{12}$ is $C_{1-3}$ substituted alkyl and $R_{15}$ is hydroxyl, then $R_7$ comprises a $C_4$ or $C_5$ unsubstituted cycloalkyl, or $R_8$ is —$OR_9$ or $R_8$ is —$NHR_{10}$, wherein $R_{10}$ is methyl substituted with a phenyl, optionally further substituted with a halogen.

18. The pharmaceutical composition of claim 17, wherein the composition comprises (R)-N-cyclohexyl-3-((3,4-dichlorophenethyl)amino)-N-(2-((2-hydroxy-2-(3-oxo-3,4-dihydro-2H-benzo[b][1,4]oxazin-8-yl)ethyl)amino)ethyl)-propanamide, (S)-N-cyclohexyl-3-((3,4-dichlorophenethyl)amino)-N-(2-((2-hydroxy-2-(3-oxo-3,4-dihydro-2H-benzo[b][1,4]oxazin-8-yl)ethyl)amino)ethyl)-propanamide, or a pharmaceutically acceptable salt thereof.

\* \* \* \* \*